United States Patent [19]

Gregorovich et al.

[11] 4,070,366

[45] Jan. 24, 1978

[54] ALKYLATION PROCESS

[75] Inventors: Basil V. Gregorovich, Maple Shade, N.J.; Stewart F. MacDonald, Ottawa, Canada

[73] Assignee: Canadian Patents & Development Limited, Calif.

[21] Appl. No.: 597,330

[22] Filed: July 21, 1975

Related U.S. Application Data

[63] Continuation of Ser. No. 281,624, Aug. 18, 1972, abandoned, which is a continuation-in-part of Ser. No. 832,001, June 10, 1969, abandoned.

[30] Foreign Application Priority Data

June 12, 1968 Canada .................................. 022,379

[51] Int. Cl.² .................. C07D 207/34; C07D 207/32
[52] U.S. Cl. ................ 260/313.1; 260/326.2; 260/326.25; 260/326.27; 260/326.46; 260/326.5 J; 260/621 R; 260/671 M

[58] Field of Search ............ 260/326.2, 313.1, 326.5 J, 260/326.46

[56] References Cited

U.S. PATENT DOCUMENTS 3,271,465   9/1966   Krewer et al. ...................... 260/651

*Primary Examiner*—Richard J. Gallagher
*Assistant Examiner*—Mary C. Vaughn
*Attorney, Agent, or Firm*—Stevens, Davis, Miller & Mosher

[57] ABSTRACT

Substituted pyrrole compounds, such as 3-ethyl-4-methyl-5-carbethoxy pyrrole, 2,4-dimethyl-3-acetyl pyrrole and 2-methyl-5-carboxy pyrrole-4-propionic acid diethyl ester, are alkylated in a single step by reaction with an aldehyde or ketone in the presence of both an acid condensing agent such as hydriodic acid and a compatible reducing agent such as metallic zinc or stannous chloride. Suitable carbonyl reactants include formaldehyde, paraldehyde, isobutyraldehyde, acetone, cyclohexanone and methyl-isobutyl ketone.

7 Claims, No Drawings

ALKYLATION PROCESS

This application is a continuation application of U.S. application Ser. No. 281,624 filed Aug. 18, 1972, now abandoned, which is a continuation-in-part application of U.S. application Ser. No. 832,001, filed June 10, 1969, now abandoned.

The present invention relates to ring alkylation of aromatic compounds and in particular relates to a novel reductive alkylation process which involves condensation of a carbonyl compound with said aromatic compound in the presence of both an acid condensation agent and a compatible reducing agent, the latter effecting reduction of the intermediate compound resulting from the condensation concurrent with its formation.

At the present time there are numerous methods of effecting ring alkylation of aromatic compounds, inter alia according generally to the following reaction sequence $$ArH_n \rightarrow Ar(CHR^1R^2)_mH_{n-m}$$

wherein Ar is an aryl group bearing $n$ replaceable ring hydrogen atoms, $m$ is an integer from 1 to $n$, and $R^1$ and $R^2$ are hydrogen or aliphatic radicals.

One known method of ring alkylation of an aromatic compound is to subject the aromatic compound to chloro-methylation by reacting the aromatic compound with formaldehyde in the presence of hydrochloric acid and zinc chloride and reducing the resultant chloromethyl intermediate such as by catalytic reduction. The process is believed to proceed according to the following reaction sequence

$$ArH_n \xrightarrow{CH_2O, HCl}_{ZnCl_2} ArH_{n-m}(CH_2Cl)_m$$
$$\xrightarrow{reduction} ArH_{n-m}(CH_3)_m$$

However, this process is subject to many disadvantages and in particular it has seldom been possible to use aldehydes and ketones other than formaldehyde thus making the process only useful for methylation. Further the process is a two stage process, of which the first stage of chloromethylation is not applicable to very reactive compounds such as many phenols, tars tending to be formed; and thus the intermediate chloromethyl substituted aromatic compound is not isolatable for subsequent reduction in the second stage. Further the presence of a chloromethyl group on the aromatic ring tends to reduce the reactivity of the other ring positions and in the majority of cases it is difficult to substitute the ring by more than one chloromethyl group and at most it has only been possible to substitute the ring by three such chloromethyl groups. It has not heretofore been possible to use this reaction for substituting the ring by more than three methyl groups and the method has usually been restricted to mono-methylation of the ring only for a single two stage process, the total two stages of the process having to be repeated to obtain further methyl nuclear substitution.

Another known process for ring alkylation of an aromatic compound is the formation from the aromatic compound of an intermediate aldehyde or ketone therefrom such as by the Freidel-Crafts or related reaction in which for example a phenol or a phenolic ether is condensed with an acid chloride or acid anhydride in the presence of aluminum chloride and subsequent reduction of the aldehyde or ketone by the Clemmensen Reduction or other method. The process is believed to proceed by the following reaction sequence

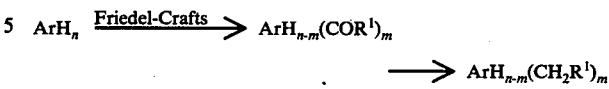
$$ArH_n \xrightarrow{Friedel-Crafts} ArH_{n-m}(COR^1)_m$$
$$\longrightarrow ArH_{n-m}(CH_2R^1)_m$$

where Ar, $n$, $m$ and $R^1$ are as above. However, again this is a two stage process involving the isolation of the intermediate aromatic aldehyde or ketone. Further it is only possible by this method to substitute the ring by at most two alkyl groups and usually one alkyl group, and again with this method it is only possible to substitute the ring with groups having $CH_2$ next to the ring.

A further known method of ring alkylation of aromatic compounds involves the treatment of the aromatic compound with formaldehyde in the presence of an acid and treatment of the product obtained with zinc dust in the presence of an alkali. This process is believed to proceed according to the following reaction sequence

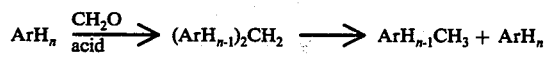
$$ArH_n \xrightarrow{CH_2O}_{acid} (ArH_{n-1})_2CH_2 \longrightarrow ArH_{n-1}CH_3 + ArH_n$$

where Ar and $n$ are as above. However, this process is also a two stage process and is only applicable to very reactive phenols such as phloroglucinol and β-naphthol and has been used for methylation only. Further, due to the mechanics of the reaction in which the intermediate compound on reaction with the zinc dust and the alkali splits into a methylated aromatic compound and a reactant non-methylated compound, a mixture of such products is obtained and complete conversion of the aromatic compound to a ring methylated compound is impossible even with recycling.

Yet another known method of ring alkylating an aromatic compound involves the Mannich reaction which comprises condensation of the aromatic compound with the hydrochloride of dimethyl amine and formaldehyde and the intermediate dimethylaminomethyl compound is subsequently subjected to catalytic reduction. The process is believed to proceed according to the following reaction sequence

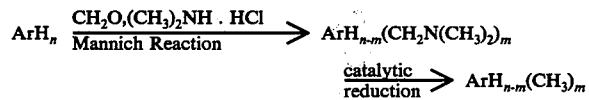
$$ArH_n \xrightarrow{CH_2O,(CH_3)_2NH \cdot HCl}_{Mannich\ Reaction} ArH_{n-m}(CH_2N(CH_3)_2)_m$$
$$\xrightarrow{catalytic}_{reduction} ArH_{n-m}(CH_3)_m$$

where Ar, $n$ and $m$ are as above. Again this process is a two-stage process involving isolation of the intermediate amino compound and is only applicable to more reactive aromatic compounds (which does not include benzene), is usually applied to methylation only and will at most allow trialkylation of the aromatic ring and usually only mono-alkylation.

A still further known method of ring alkylation of an aromatic compound is by means of the Grignard Reaction applied to the aromatic compound and treatment of the Grignard compound so obtained with dimethyl sulphate. The process is believed to proceed according to the following reaction sequence

Again this process is a two stage process involving an intermediate Grignard compound and this process is not applicable to compounds which do not give Grignard reagents such as phenol and with this method it is only possible to monoalkylate the ring.

It is also known that ring alkylation may be carried out by treatment of the aromatic compound with an alcohol or an alkene in presence of a strong acid at a temperature from about 0° to 100° C. The process is believed to proceed according to the following reaction sequence

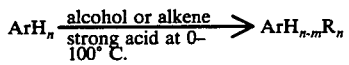

where Ar and $n$ are as above and R is an aliphatic or araliphatic radical. While this process is a single stage process it has limited usefulness as rearrangement of the alkyl group of the alkylating reagent may take place and in particular reaction with secondary butyl alcohol frequently gives tertiary butyl derivatives. Further methylated benzenes may isomerize or disproportionate during the reaction, for instance to benzene and poly-methylbenzenes. The reaction is also reversible and as such complete alkylation is rarely if ever achieved.

Another known single step process for the production of ring alkyl aromatic compounds is treatment of the aromatic compound with an alcohol or alkene and the presence of a solid catalyst at high temperatures. The process is believed to proceed according to the following reaction sequence

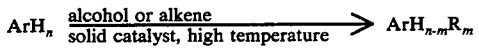

where Ar, R, $n$ and $m$ are as above. This method is subject to the similar disadvantage as the previous method and in addition only stable and volatile aromatic compounds may be alkylated.

Again another known single stage process for the alkylation of aromatic compounds involves the Friedel-Crafts reaction using aluminum chloride and an aliphatic chloro-compound. The process is believed to proceed according to the following reaction sequence

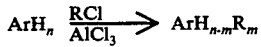

where Ar, R, $n$ and $m$ are as above. Again the disadvantages of the previous process occur.

Finally, the ring alkylated aromatic compounds may be prepared in a known single stage by reacting the aromtic compounds at a temperature of about 220° C. with an alcohol and the potassium salt of the alcohol according to the following reaction sequence

where Ar, R $n$ and $m$ are as above. This process, however, needs high pressure, is only applicable to very reactive compounds such as pyrroles and β-naphthol, and the latter is only mono-methylated. Further labile groups such as ethoxy carbonyl and acetyl are usually split off such as for instance in the cases of pyrroles due to the high temperature used in the process.

In summary therefore, all the heretofore known processes are subject to substantial disadvantages in their applicability to the akylation of aromatic compounds and many involve two stage procedures with isolation of the intermediate and those which do not are frequently accompanied by isomerization. The known one stage process which avoids these disadvantages, alkylation with an alcohol and its potassium salt under pressure at about 220° C. is only applicable to very reactive aromatic compounds.

The present invention provides a process for the ring alkylation of aromatic compounds such as benzenes, phenols and pyrroles in which the intermediates are not isolated but are reduced as formed or by a continuation of the conditions under which they are formed. As a result, very reactive intermediates are reduced rather than being converted into tars and any starting material regenerated by reduction of the intermediates, and any partially alkylated products are automatically recycled to ensure complete alkylation.

According to the present invention, therefore, there is provided a method of ring alkylating an alkylatable aromatic compound with comprises reacting said compound with a carbonyl compound or a compound generating said carbonyl compound under the reaction conditions in the presence of an acid condensing agent and a reducing agent, said aromatic compound and said carbonyl compound being stable under the reaction conditions and said aromatic compound having at least one position on the ring having replaceable hydrogen or bearing a substituent removable under the reaction conditions to yield a replaceable hydrogen atom whereby to form with said carbonyl compound a reducible intermediate compound which is reduced to an alkyl derivative of said aromatic compound.

Thus, according to the present invention the reducing agent is present from the start of the reaction and thus, the intermediate condensation products of the carbonyl compound with the aromatic compounds are automatically reduced, rather than going to tars. This has the advantage that is not necessary to isolate the intermediate, i.e., the products of the condensation, prior to their reduction which is frequently unworkable because the intermediates are undoubtedly various, often mixtures, and sometimes unstable. Again as the groupings on the aromatic ring formed by the condensation reaction are reduced to alkyl groups, while conditions permitting further condensations are maintained, this allows for poly-substitution of the ring for alkyl groups activate the ring and thus facilitate further condensation. Further, it has been found that alkylation can be carried out with the process of the present invention even when the first stage of the reaction, e.g., chloromethylation, has heretofore failed because the intermediate product is so reactive that it normally goes to tar etc., the simultaneous presence of the acid condensing agent and the reducing agent apparently stabilizing the intermediate until it is reduced. Thus even reactive aromatic compounds do not revert to tars before the groupings are reduced. Finally, as will be readily seen where the intermediate upon being reduced forms a mixture of the final product and the starting material then the starting material is automatically present for further reaction with the carbonyl compound to reform the intermediate and thus there is automatic recycling of the unreacted starting material. It is therefore possible by means of the process of the present invention to achieve substantially complete conversion. Thus, as both the condensation and the reduction can proceed throughout, any reduction product which is not the product desired e.g. the regenerated reactant aromatic compound or a partially alkylated aromatic compound is automatically recycled to the process for further condensation with the carbonyl compound and reduction of the condensation product.

The process of the present invention is applicable to and has advantage with inter alia the following reaction mechanisms which ae illustrated using hydriodic acid as the acidic condensating agent and the reducing agent and in which Ar is an aryl group and R is an alkyl group

  (I)

In the above monoalkylation reaction (I) the process of the present invention has the advantage of eliminating the isolation of the intermediate and is much more convenient than the conventional two stage process. Further the process of the present invention has the particular advantage that it can operate even with the formation of intermediate products which were in the conventional two stage process unstable to an extent that the conventional two stage process was inoperable.

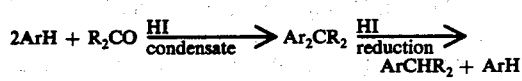  (II)

In the above monoalkylation reaction (II) in addition to the advantages with reaction (I) the process of the present invention also recycles the regenerated aromatic compound ArH for subsequent condensation and thus obtain complete monoalkylation. This cannot be achieved in the conventional two stage process. This feature is particularly advantageous as there is no way of knowing a priori whether on monoalkylation the intermediate condensate product will be as in reaction (I) or reaction (II).

  (III)

In this complete polyalkylation reaction (III) the partially alkylated products are automatically recycled for further condensation and reduction until complete polyalkylation is achieved. Thus the advantages of the process of the present invention in respect to reaction (II) also accrue to the process of the present invention in respect of reaction (III). Further, the reduced lower alkyl groups —$CHR_2$ such as —$CH_3$ and $CH_2Cl$ facilitate the introduction of further substituents, e.g. $CIR_2$ during condensation and thus aid in completing the polyalkylation. On the other hand the unreduced substituents e.g. $CIR_2$ retard introduction of further such substituents and thus in the conventional two stage process it is only possible to introduce a limited number of alkyl groups into the ring per cycle.

In particular, therefore, in the process of the present invention the condensation and reduction stages automatically repeat until all the replaceable hydrogen in the aromatic nucleus are replaced by alkyl groups whether or not they have been reformed by the reduction stage.

It is essential for the process of the present invention that both the aromatic compound and the carbonyl compounds are stable under the reaction condition, i.e. condensation takes place before any undesirable changes take place in the reactant compounds, e.g. before the reactant compounds undergo ring opening or generally decomposition and as the reaction conditions involve acidic conditions, it is generally desirable that the compounds should be stable under acidic conditions. Further it is necessary that the aromatic compound and carbonyl compound be reactive enough to condense and in particular for the aromatic compound to have one or more replaceable hydrogen atoms so as to be reactive with the carbonyl compound under the reaction conditions to form the intermediate. However, the aromatic compound may have present groups such as certain acyl, halogen, carbethoxy and carboxy groups which are automatically removed under the reaction conditions such as elevated temperature, thus generating the aromatic compounds having replacement hydrogen atoms in situ during the reaction. Further the aromatic compound must form with the carbonyl compound a reducible condensation intermediate compound as it is essential to the reaction that there be reduction of the intermediate. Suitable aromatic compounds therefore, include heterocyclic aromatic compounds which are five membered ring compounds containing nitrogen in the ring and in particular derivatives of pyrrole as well as six membered carbocyclic compounds including benzene and derivatives thereof. Thus, in particular, the heterocyclic aromatic compound may be pyrrole substituted by at least one and preferably two methyl groups with or without acetyl groups and/or carbethoxy groups. The carboxy, carbethoxy or acetyl groups are removable from the pyrrole derivative at elevated temperatures above about 100° C. and if it is desired to substitute the positions normally held by these groups by alkyl groups then the reaction may be conducted at the elevated temperature necessary to remove these groups. Particular pyrrole derivatives which may be mentioned as aklylatable by the method of the present invention include 2,4-dimethyl-5-carbethoxy pyrrole, 2,4-dimethyl-3,5-dicarbethoxy pyrrole, 2-methyl-3 carbethoxy pyrrole, 2,4-dimethyl-3-acetyl pyrrole, 2-carbethoxy-3-methyl-pyrrole, 2-methyl-5-carbethoxy pyrrole, 2,3-dimethyl-5-carbethoxy pyrrole, 2,4-dimethyl-3-bromo-5-carbethoxy pyrrole, 3-ethyl-4-methyl-5-carbethoxy pyrrole, 3-methyl-4-carbethoxy pyrrole, 2,5-dimethyl-3-carbethoxy pyrrole, 2-methyl-3,5-dicarbethoxy pyrrole, 3-methyl-2,5-dicarbethoxy pyrrole, 2,3-dimethyl-5-carbethoxy pyrrole, 2,3-dimethyl pyrrole, 2,5-dimethyl pyrrole, 2-methyl-5-carboxy pyrrole-4-propionic acid diethyl ester and 2,4-dimethyl pyrrole. Suitable carbocyclic six membered aromatic compounds which may be mentioned include benzene, or benzene substituted by at least one hydroxy, methyl or chlorine group and in particular there may be mentioned benzene, xylenes, phenols, tetrahydronaphthalene or dichlorobenzenes.

The carbonyl compounds reacted with the aromatic compound are aldehydes and ketones and these may suitably have the formula $R^3COR^4$ wherein $R^3$ is hydrogen or an aliphatic grouping and $R^4$ is hydrogen or an aliphatic or aromatic grouping. In particular $R^3$ may be hydrogen or an alkyl or carboxyl group and R⁴ is hydrogen or an alkyl group or R³ and R⁴ together may form with the carbon atom to which they are attached a cycloalkylidene group. Thus, R³ is suitably methyl, ethyl, isobutyl, tert-butyl, carboxyl, β-carboxyethyl, β-acetylethyl, β-amino-ethyl or hydrogen, R⁴ is hydrogen, methyl, ethyl or 3-acetyl-4-methyl-5-carbethoxypyrryl-2- or R³ and R⁴ together with the carbon atom to which they are attached form a cyclohexylidene group. Particular carbonyl compounds which may be mentioned include formaldehyde, acetaldehyde, propionaldehyde, n-butyraldehyde, isobutyraldehyde, paraldehyde, heptaldehyde, laurylaldehyde, stearaldehyde, amino-acetaldehyde, acetone, diethyl-ketone, isobutylmethyl ketone, 3-pentanone, cyclopentanone, cyclohexanone, pyruvic acid, levulinic acid, glyoxylic acid, benzaldehyde, acetophenone, chloroacetone, 2,5-hexane dione and 2-formyl-3-acetyl-4-methyl-5-carbethoxy-pyrrole. The formaldehyde and acetaldehyde are desirably generated in situ during the course of the reaction from para-formaldehyde and paraldehyde initially added to the reaction mixture. Other compounds generating the carbonyl compounds include acetals such as amino acetaldehyde, dimethyl acetal and 2-biphenyl-carboxaldehyde, diethylacetal and, a trimer of stearaldehyde.

The condensing agent used in the process of the present invention is an acid such as hydriodic acid, and hydrobromic acid, sulfuric acid, hydrochloric acid. The condensation is usually carried out in the presence of a solvent which may also be acidic such as acetic acid and particular condensing agent/solvent systems which may be mentioned include hydriodic acid, hydrogen iodide in acetic acid, hydrogen bromide in acetic acid, hydrogen chloride in acetic acid and sulfuric acid in acetic acid.

In the process of the present invention any reducing system which is compatible with the condensing agent and capable of reducing the intermediate to the final alkylated product may be used and typical reducing agents which may be mentioned include hydrogen iodide solutions, zinc, zinc amalgam or stannous bromide or chloride. In conjunction with the hydrogen iodide there may be present red phosphorus, phosphonium iodide or hypophosphorous acid which tend to increase the effectiveness of the hydrogen iodide by reconverting the iodine formed during the reduction back to hydrogen iodide. In will be readily seen that hydriodic acid being both a reducing agent and an acid may serve both purposes in the process of the present invention, i.e. the reaction of the carbonyl compound with the aromatic compound may be effected in hydriodic acid alone.

The precise conditions of reaction are not critical and depend primarily upon the reactant carbonyl compound and reactant aromatic compound and as such the reaction may be conducted at elevated or normal temperature and usually under atmospheric pressure. However, in some cases carbethoxy groups can be either retained on the ring by alkylation at lower temperatures or split off and replaced by alkyl groups by alkylating at higher temperatures. The reaction may be conducted in the presence or absence of a solvent as is convenient but is normally conducted in the presence of a solvent such as acetic acid.

The present invention will be further illustrated by way of the following Examples in which the aqueous hydriodic acid used had a density of about 1.94, had been decolourized with phosphonium iodide and when the temperature of the reaction is not indicated there was a rise to 30° or 40° C. consequent on the use of magnetic stirring. Melting points are corrected and the nmr spectra of all the products were consistent with the structures assigned, the Beilstein tests for halogen were negative, and the pyrroles gave positive Ehrlich reactions hot.

EXAMPLE 1

Preparation of Hexamethylbenzene from Benzene

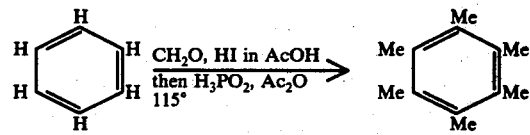

Hydrogen iodide in acetic acid (20 ml, density 1.6, about 50%), 3 g of paraformaldehyde and 1 ml of benzene were stirred at 20° C for 18 hours in a stoppered flask, then heated for 18 hrs at 90° C. under a reflux condenser. The mixture was cooled, 5 ml of 50% hypophosphorous acid and 20 ml of acetic anhydride were added, and heating continued for 4 hrs at 110° C. It was again cooled, 5 ml of hypophosphorous acid added, and again heated for 18 hrs at 115° C. The mixture was cooled somewhat, decolorized with hypophosphorous acid, and poured into water. The solid which separated was dried, boiled with 10 ml of pyridine, recovered by pouring the mixture into water, ground and washed with 20 ml of methanol, dried, sublimed (about 100° C. 0.1 mm), and crystallized from 25 ml of methanol as colourless plates (589 mg), m.p. 165°–166.5° C. (lit[1] 166.6°) after changing to needles or prisms at ca 105° C. and to plates at ca 145° C. A further 45 mg were obtained from the methanolic mother liquor (total 635 mg. 35%). No aromatic protons were apparent in the nmr spectrum when the intensity was increased 100 times. Anal. Calc. for $C_{12}H_{18}$: C, 88.82; H, 11.18. Found: C, 88.63; H, 11.10.

[1] H. A. Smith and E. F. H. Pennekamp, J. Am. Chem. Soc., 67, 279 (1945).

EXAMPLE 2

Preparation of Hexamethyl benzene from p-xylene

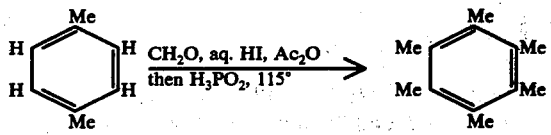

Hexamethylbenzene was obtained similarly, but more conveniently and in 82% yield, from p-xylene (1 ml), 10 ml of aqueous hydriodic acid, 40 ml of acetic anhydride and 2 g of paraformaldehyde, at 90° C. then at the boiling point of the mixture.

EXAMPLE 3

Preparation of Pentamethylphenol from Phenol

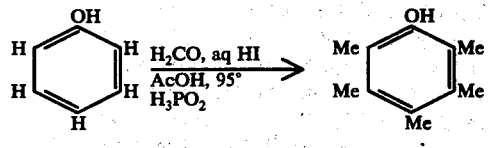

To phenol (4.06 g) in acetic acid (40 ml) was added hydriodic acid (43 ml) and paraformaldehyde (6.47 g). The mixture was kept at 95° C. under nitrogen and stirred for six hours, adding 50% hypophosphorous acid periodically to decolourize it. Ammonium hydroxide was then added dropwise to the cooled (0° C.) and stirred solution until it was basic (pH~8). The product was extracted with ether (3 × 30 ml), which was dried over anhydrous magnesium sulfate, filtered, and then removed in vacuo to leave the crude product (2.1 g). Several recrystallizations from n-hexane gave the product, 1.64 g (25%), m.p. 127°–129° C. (lit.[2] 125° C.). The infrared spectrum had the hydroxyl absorption at 3625 cm$^{-1}$.

Analysis: Calc. for $C_{11}H_{16}O$: C, 80.44; H, 9.83; mol. wt. 164. Found: C, 80.12; H, 9.91; mol. wt.160 (vap. press), 164 (Mass spec.).

2. A. W. Hofmann, Berichte, 18, 1826 (1885).

EXAMPLE 4

Preparation of 2,3,4-Trimethyl-5-carbethoxy-pyrrole

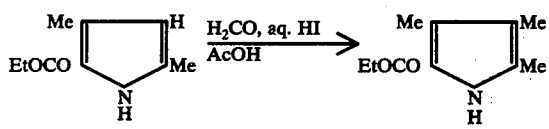

2,4-Dimethyl-5-carbethoxy-pyrrole (0.83 g), acetic acid (10 ml), hydriodic acid (10 ml) and paraformaldehyde (0.60 g) were stirred 3 hours at 25° C. under nitrogen. Hypophosphorous acid (50%, about 1 ml) was added, dropwise to decolourize the solution. The cooled solution (0° C.) was made basic with ammonium hydroxide and the product was extracted with ether (2 × 20 ml). The extract was dried over magnesium sulfate, filtered, and the ether removed in a rotating evaporator at 20° C. Recrystallization of the residue from benzene gave the product, 0.58 g (64%), m.p. 125°–126° C. (lit[3] m.p. 126° C.).

Analysis, Calc. for $C_{10}H_{15}O_2N$: C, 66.27; H, 8.34; N, 7.73 Found: C, 66.35; H, 8.18; N, 7.90.

3. H. Fischer and B. Wallach, Annalen der Chemie, 450, 125 (1926).

EXAMPLE 5

Preparation of Tetramethylpyrrole

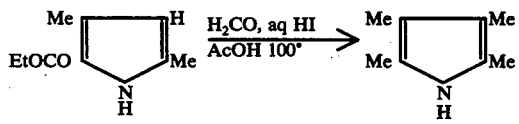

2,4-Dimethyl-5-carbethoxy-pyrrole (1.64 g), acetic acid (25 ml), aqueous hydriodic acid (25 ml) and paraformaldehyde (0.589g), were heated at 95°–100° C. for three hours under nitrogen with stirring. The work up was the same as that of 2,3,4-trimethyl-5-carbethoxy-pyrrole in Example 4 except the 2 × 75 ml of ether was used and care was taken to avoid exposure of the product to air. It was purified by distillation (10 mm, 60° C.) to give 0.628 g (52%), m.p. 106°–108° C. (lit[4] m.p. 111°–112° C.).

Anal., Calc. for $C_8H_{13}N$: C, 77.99; H, 10.64; N, 11.37, Found: C, 77.88; H, 10.51; N, 11.22.

4. H. Fischer and E. Bartholomaus, Z. physiol Chem., 80, 10 (1912)

EXAMPLE 6

Preparation of 2,4-Dimethyl-3-acetyl-5-n-Propyl-pyrrole

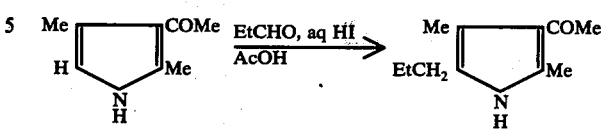

2,4-Dimethyl-3-acetyl-pyrrole (1.02 g), acetic acid (15 ml), aqueous hydriodic acid (25ml) and propionaldehyde (1.74g), were stirred at 25° C. three hours under nitrogen. The work up was the same as that of 2,3,4-trimethyl-5-carbethoxy-pyrrole in Example 4 except that 2 × 50 ml ether were used. Recrystallization from benzene gave the product 0.786 g (59%) m.p. 157°–158°C.

Anal. Calc. for $C_{11}H_{17}ON$: C, 73.70; H, 9.56; N, 7.81; Found: C, 73.73; H, 9.39; N, 7.79.

EXAMPLE 7

Preparation of 2,4-Dimethyl-3-acetyl-5-isopropyl-pyrrole

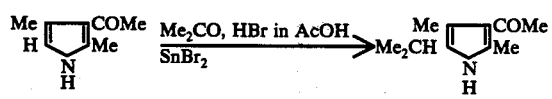

Anhydrous stannous bromide (5g) was stirred to solution in 20 ml of hydrogen bromide in acetic acid (30–32 %). 2,4-Dimethyl-3-acetyl-pyrrole (548 mg) was added and the mixture was warmed to dissolve this, then cooled to 30° C. Acetone(0.6 ml) was added and the solution was stirred at 35° C. for 2½ hrs then poured into water at 10° C. The product was separated and washed with dilute hydrochloric acid then with water. It formed colourless micro-prisms (549 mg. 77%), m.p. 166°–167° C. or 173–174.5° C. after changing to cubes at about 136° C. For analysis it was recrystallized from aqueous ethanol as prismatic rods, m.p. 172° C.

Calc. for $C_{11}H_{17}NO$: C, 73.70; H, 9.56; N, 7.81. Found: C, 73.92; H, 9.23; N, 7.88.

Example 8

Preparation of 2,4Dimethyl-3-acetyl-5-isopropyl pyrrole

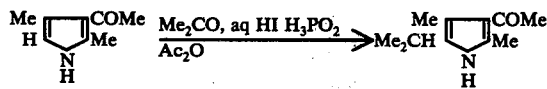

Aqueous hydriodic acid (10 ml) and 2 ml of 50% hypophosphorous acid were cooled and stirred while 10 ml of acetic anhydride was slowly added. 2,4-Dimethyl-3-acetyl-pyrrole (548 mg) was dissolved in the solution, 0.6 ml of acetone added, and the mixture was stirred for ½ hr. by which time a yellow precipitate had formed and redissolved and the solution had turned yellow; the final temperature was 37° C. It was poured into 100 ml of water and 30 ml of ammonium hydroxide kept at 20° C. The nearly colourless product separated as plates (662 mg, 92%). At 138° C. these changed to cubes which either melted at 165° C. or turned to irregular needles, m.p. 171°–173° C. For analysis, it was recrystallized from aqueous ethanol as colourless plates, m.p. 165.5° C. or 171.5°–173° C.

Anal. Found: C, 73.59; H, 9.48; N, 7.76.

EXAMPLE 9

Preparation of 2,4-Dimethyl-3-acetyl-5-benzyl-pyrrole

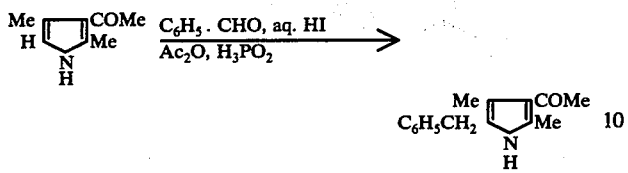

A solution of 10 ml of aqueous hydriodic acid, 10 ml of acetic anhydride and 2 ml of 50% hypophosphorous acid containing 548 mg of 2,4-dimethyl-3acetyl pyrrole was stirred magnetically while a solution of 0.6 ml of benzaldehyde in 5 ml of acetic anhydride was slowly added over 20 mins. The solution was stirred for 10 mins, then poured into water. The crude product which separated was recrystallized from acetone (thimble) as nearly colourless irregular plates (85%, m.p. 165.5°–167° C. after a partial change to prismatic rods above 165° C. Anal. Cal. for $C_{15}H_{17}NO$: C, 79.26; H, 7.54; N, 6.16. Found: C, 79.22; H, 7.50; N, 6.18.

EXAMPLE 10

Preparation of 2,4-Dimethyl-3-acetyl-5-(α-methyl-benzyl)-pyrrole

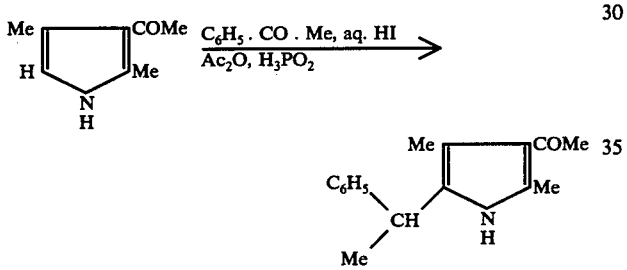

A solution of 0.6 ml of acetophenone of 5 ml of acetic anhydride was slowly added to a stirred mixture of 10 ml of aqueous hydriodic acid, 10 ml of acetic anhydride and 2 ml of hypophosphorous acid containing 548 mg of 2,4-dimethyl-3-acetyl pyrrole. The mixture was allowed to stand for two days at room temperature then poured into water. The crude product which separated was recrystallized from acetone (thimble) as nearly colourless rhombic plates (75%), mp. 146°–148.5° C. Anal. Calc. For $C_{16}H_{19}NO$: C, 79.63; H, 7.94; N, 5.80. Found: C, 79.47: H, 7.78; N, 5.79.

EXAMPLE 11

2,4-Dimethyl-3-acetyl-5-cyclohexyl-pyrrole

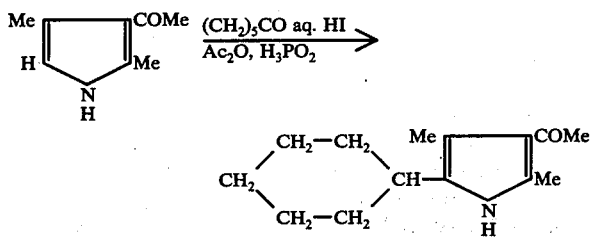

A solution of 10 ml of aqueous hydriodic acid, 10 ml of acetic anhydride and 2 ml of 50% hypophosphorous acid was stirred magnetically at 40° C. while 548 mg of 2,4-dimethyl-3-acetyl-pyrrole were dissolved in it, 0.5 ml of cyclohexanone was then added, and an additional 0.5 ml of cyclohexanone was added after a few minutes'. The solution was stirred at 40° C. for 1½ hrs. then poured into water. The crude product which separated, m.p. 186°–188° C. was recrystallized from ethanol as colourless rhombic prisms (82%), m.p. 188.5°–189° C. after changing to flat prisms above 153° C.

Anal. Calc. for $C_{14}H_{21}NO$: C, 76.66; H, 9.65; N, 6.39. Found: C, 76.49; H, 9.50; N, 6.30.

EXAMPLE 12

2,4-Dimethyl-3-acetyl-5-(1-carboxy-ethyl)-pyrrole

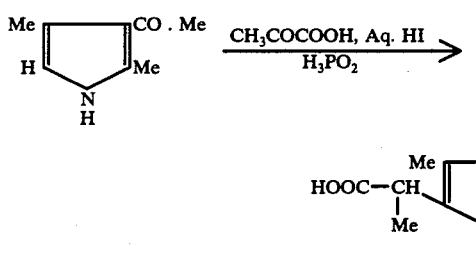

A solution of 548 mg. of 2,4-dimethyl-3-acetyl-pyrrole in 10 ml of hydriodic acid and 2 ml of 50% hypophosphorous acid was treated with 0.4 ml of pyruvic acid and stirred for 10 min, when yellow crystals separated. After standing for 2 days at 0° C. the crystals were separated, dried and slurried with 5 ml of water. The resulting colourless product was separated, washed with water, dried and recrystallized from ether (thimble) as pale yellow plates (46%), m.p. 156°–158° C. (dec.).

Anal. Calc. for $C_{11}H_{15}NO_3$: C, 63.14; H, 7.23; N, 6.69; eq. wt. 209. Found: C, 63.11; H, 6.98; N, 6.80; eq. wt. 207.

EXAMPLE 13

3,5,4'-Trimethyl-4,3'-diacetyl-5'-carbethoxy-dipyrryl methane

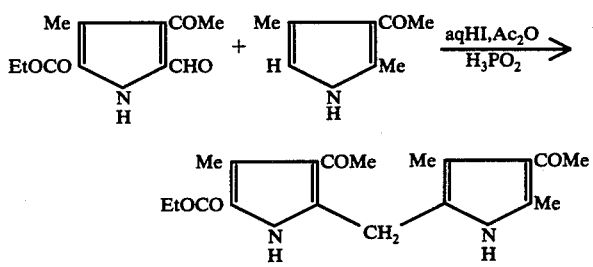

Hydriodic acid (10 ml) was stirred and cooled while 10 ml of acetic anhydride were added slowly, Hypophosphorous acid (2 ml, 50%) and 548 mg of 2,4-dimethyl-3-acetyl-pyrrole were added and the mixture was stirred at room temperature until the latter dissolved. 2-Formyl-3-acetyl-4-methyl-5-carbethoxy-pyrrole (892 mg) was added and the mixture was stirred at 40°–45° C. for 2 hours, then poured into 150 ml of water. The precipitate was separated, dried, slurried and filtered with 15 ml of ethanol, dried, and extracted into 40 ml of acetone (thimble). Th product (781 mg) crystallized from the acetone of colourless plates, m.p. 209°–212° C. (lit[5] 210°), and concentrating the acetone gave a further 219 mg (total, 73%). The X-ray powder photograph and the nmr spectrum were identical with those of authentic material prepared according to Schlesinger et al.[5], for which we found the m.p. to be 210°-213° C. The mixed mp. was 209°-213° C.

Anal. Calc. for $C_{19}H_{24}O_4N_2$: C, 66.26; H, 7.02; N, 8.13; OEt, 13.08. Found: C, 66.11; H, 7.23; N, 8.18; OEt, 12.97.

[5]. W. Schlesinger, A. H Corwin and L. J. Sargent, J. Am. Chem. Soc., 72, 2871 (1950).

EXAMPLE 14

2,4-Dimethyl-3-isobutyl-5-carbethoxy-pyrrole

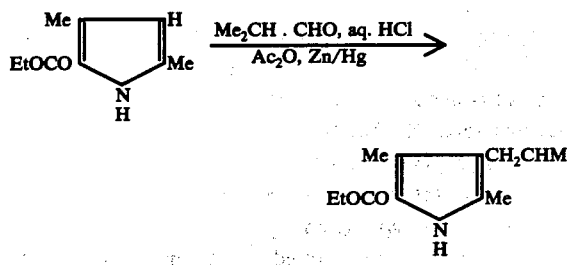

Acetic anhydride (20 ml) was slowly added to 5 ml of concentrated hydrochloric acid with stirring and cooling and 668 mg of 2,4-dimethyl-5-carbethoxy-pyrrole were dissolved in the resulting solution. Amalgamated zinc (10 gm, 20 mesh) and 0.75 ml of iso-butyraldehyde were then added at 20°, and the mixture was stirred for 15 minutes at 20°-25° C. The zinc was separated, washed with acetic acid, and the liquids were poured into water to precipitate the crude product. It was dried and extracted into pentane (thimble), the pentane was evaporated, and the residue was recrystallized from aqueous ethanol (13 ml of 55%) as colourless needles (681 mg), m.p. 115°-117° C (lit[6] 116°-117° C.) after changing to fine needles at about 112° C. and to plates at about 115° C. A further 51 mg were obtained from the mother liquors (total 732 mg, 82%). The nmr spectrum and the X-ray powder photograph were identical with those of authentic material, and the mixed m.p. was 115°-117° C.

Anal. Calc. for $C_{13}H_{21}NO_2$: C 69.92; H, 9.48; N, 6.27. Found: C, 70.08; H, 9.67; N, 6.25.

[6]. J. L. Archibald, D. M. Walker, K. B. Shaw, A. Markovac and S. F. MacDonald, Canad. J. Chem., 44, 345 (1966)

EXAMPLE 15

2,4-Dimethyl-3-acetyl-5-neopentyl-pyrrole

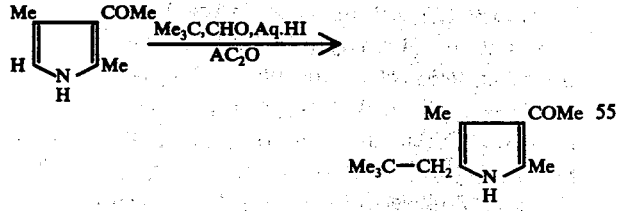

2,4-Dimethyl-3-acetyl-pyrrole (548 mg) was warmed to solution in a mixture of 10 ml of aqueous hydriodic acid, 10 ml of acetic anhydride and 2 ml of hypophosphorous acid. The solution was cooled to 35° C. and 0.85 ml of pivalaldehyde were added. The solution was stirred for ten minutes, by which time the initially dark brown color had changed to yellow, then poured into 125 ml of water. The product separated as a colourless powder (769 mg, 93%), m.p. 156°-163 ° C. For analysis, it was recrystallized from ether-pentane, sublimed at 115° C. ($10^{-4}$ mm), and again recrystallized by extraction into hexane (thimble) as long colourless plates, m.p. 166°-167° C. after changing to prisms below 130° C.

Anal. Calc. for $C_{13}H_{21}NO$: C, 75.31; H, 10.21; N, 6.76. Found: C, 75.13; H, 10.30; N, 6.58.

EXAMPLE 16

2,4-Dimethyl-3-acetyl-5-(4-methyl-2-pentyl)-pyrrole

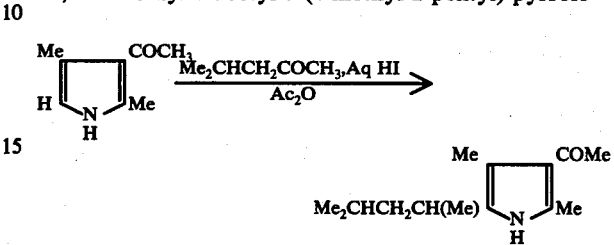

Methyl-isobutylketone (1.1 ml) was added to a solution of 548 mg of 2-4-dimethyl-3-acetyl-pyrrole in aq. hydriodic acid (10 ml), acetic anhydride (10 ml) and hypophosphorous acid (2ml). The solution was stirred for four hours; then poured into a mixture of 150 ml of water and 30 ml of ammonium hydroxide. The product separated as tiny colourless prisms (709 mg, 80%), m.p. 140°-141.5° C. For analysis, it was recrystallized from aqueous ethanol (charcoal) as tiny colourless prisms, m.p. 142°-143° C. some changing to plates at 120° C. Anal. Calc. for $C_{14}H_{23}NO$: C, 75.97; H, 10.47; N, 6.33. Found C, 75.81, H, 10.37; N, 6.38.

EXAMPLE 17

2,4-Dimethyl-3-acetyl-5-(3-pentyl)-pyrrole

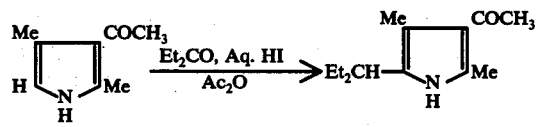

3-Pentanone (0.85 ml) was added to a solution of 548 mg of 2,4-dimethyl-3-acetyl-pyrrole, in 10 ml of aq. hydriodic acid, 10 ml of acetic anydride and 2 ml of hypophosphorous acid. The solution was stirred for 1¾ hours then poured into 200 ml of water to precipitate the product as tiny nearly colourless prisms (651 mg, 79%), m.p. about 186°-189° C. For analysis it was recrystallized from ethanol as colourless plates, m.p. 188.5° C. after a solid phase change at 135°. Anal. Calc. for $C_{13}H_{21}NO$: C, 75.31; H, 10.21; N, 6.76. Found: C, 75.13; H, 10.04; N, 6.78.

EXAMPLE 18

2,4-Dimethyl-3-acetyl-Pyrrole-5-(4-pentanoic) acid

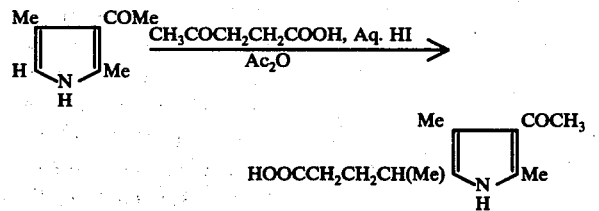

A solution of levulinic acid (0.6 ml) in 5 ml of acetic anhydride was slowly added to a solution of 548 mg of 2,4-dimethyl-3-acetyl-pyrrole in aqueous hydriodic acid (10 ml), acetic anhydride and hypophosphorous acid (2ml). The solution was stirred for twelve hours, then the volatile solvents were removed in a vacuum desiccator over potassium hydroxide. Water (10 ml) was added to the residue to yield the product as an oil which soon solidified to salmon coloured prisms (742 mg), m.p. 177°–179° C. For analysis, it was recrystallized from acetone (thimble) as nearly colourless prisms, m.p. 177°–178° C. Anal. Calc. for $C_{13}H_{19}NO_3$; C, 65.80, H, 8.07; N, 5.90; eq. wt. 237. Found: C, 66.03; 8.20; 5.91; eq. wt. 234.

EXAMPLE 19

2,5Bis-(3,5-dimethyl-4-acetyl-2-pyrryl)-hexane

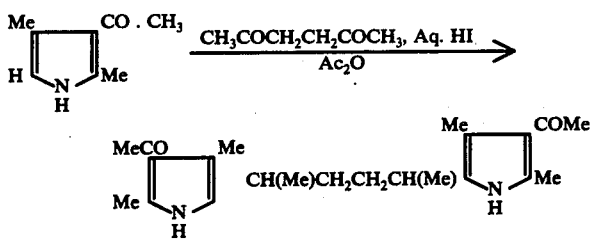

2,5-hexanedione (1 ml) was added to a solution of 548 mg of 2,4-dimethyl-3 -acetyl-pyrrole in 10 ml of aqueous hydriodic acid, 10 ml of acetic anhydride and 2 ml of hypophosphorous acid. The solution was stirred for 1½ hours then poured into 150 ml of water to precipitate the nearly colourless product (442 mg), m.p. 263°–268° C. For analysis, it was twice recrystallized from acetone (thimble) as a colourless crystalline powder, m.p. 275°–279° C. after changing to needles at 271°. Anal. Calc. for $C_{22}H_{32}N_2O_2$: C, 74.12; H, 9.05; N, 7.86. Found: C, 74.01; H, 9.04; N, 7.94.

It will be seen from the above Example that besides ring alkylation the use of dicarbonyl compounds such as 2,5-hexane dione makes it possible for the alkyl group to bridge two rings.

EXAMPLE 20

2,4-dimethyl-3-acetyl-5-ethyl-pyrrole

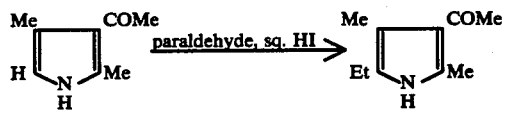

A solution of 2,4-dimethyl-3-acetyl-pyrrole (548 mg) in 10 ml of aqueous hydriodic acid containing a little solid phosphonium iodide was cooled in an ice-salt bath. Paraldehyde (0.35 ml) was added and the solution was stirred for 4½ hrs. without further cooling. The solution was then added to 100 ml of ice water to precipitate the light brown product (385 mg, 58%), m.p. 153°–160° C. For analysis, it was sublimed in vacuo then recrystallized from ether (thimble) as grey needles, m.p. 163° C. after changing to plates at 140°. Anal. Calc. for $C_{10}H_{15}O$: C; 72.69, H, 9.15; N, 8.48. Found: C, 72.67; H, 8.88; N, 8.69.

EXAMPLE 21

2,4-Dimethyl-3-acetyl-pyrrole-5-acetic acid

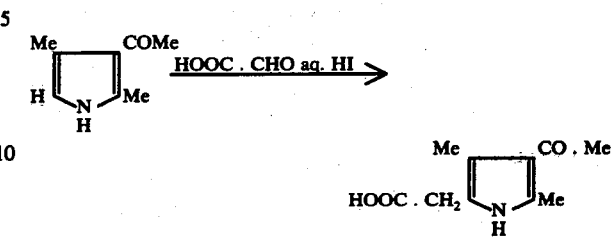

Glyoxalic acid monohydrate (500mg) was added to a solution of 548 mg of 2,4-dimethyl-3-acetyl-pyrrole in 10 ml of aqueous hydriodic acid and 2 ml of hypophosphorous acid. The solution was stirred for one hour at 15° C. The yellow crystalline solid was filtered off, washed with ether, dried, then slurried with 5 ml of water. The solid was again separated, washed with 5 ml of water, dried, and extracted into 40 ml of ether (thimble). When the ether solution was concentrated the produce separated as yellow prisms (550 mg), m.p. 195°–205° C. For analysis, it was recrystallized by dissolving it in 40 parts of cold 50% aqueous acetone, boiling off the acetone, and cooling. It separated as nearly colourless prismatic rods, m.p. 206°–210° C. after changing to prisms at 155° and evolving gas at 175°; presumably it decarboxylated to the 5-methyl derivative before melting. Anal. Calc. for $C_{10}H_{13}NO_3$: C, 61.52; H, 6.71; N, 7.18; eq. wt. 195. Found: C, 61.35: H, 6.90; N, 7.10; eq. wt. 197.

EXAMPLE 22

2,4-Dimethyl-3-acetyl-5-isopropyl-pyrrole

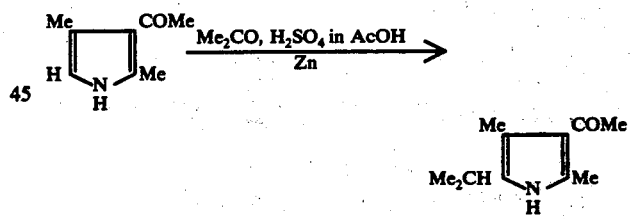

2,4-Dimethyl-3-acetyl-pyrrole (548 mg), 1 ml of acetone and 10 gm of amalgamated zinc (20 mesh) were added to a solution of 1 ml of concentrated sulfuric acid in 20 ml of acetic acid. The mixture was stirred for 1 hour at 45° C. The liquid was decanted from the zinc into 100 ml of water forming a solution from which the crude product separated at 15° C. (174 mg, m.p. 164°–169° C. after the usual solid phase changes). For analysis, it was extracted into ether (thimble) then recrystallized from 3 ml of aqueous ethanol as nearly colourless elongated prisms, m.p. 170°–172° C. (171°–173° when mixed with the product of Example 8) after a solid phase change at 142°. Anal. Calc. for $C_{11}H_{17}NO$: C, 73.70; H, 9.56; N, 7.81. Found: C, 73.60; H, 9.40; N, 7.92.

EXAMPLE 23

2,3,4,5-Tetramethyl-pyrrole

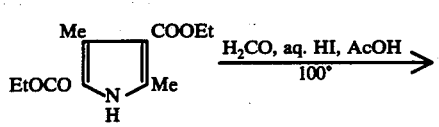

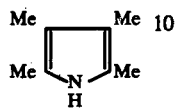

2,4-Dimethyl-3,5-dicarbethoxy-pyrrole (2.4 g), acetic acid (35 ml), aq. hydriodic acid (35 ml) and paraformaldehyde (1.2 g) were heated at 100° C. for 4 hours under a stream of nitrogen. The crude product was obtained as in Example 5 then distilled (15 mm, 65° C.) to yield 0.44 g (36%), m.p. 107°–109°.

EXAMPLE 24

2,4,5-Trimethyl-3-acetyl-pyrrole

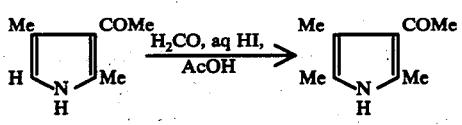

2,4-Dimethyl-3-acetyl-pyrrole (0.68 g), acetic acid (15 ml), aq. hydriodic acid (15 ml) and paraformaldehyde (0.6 g) were stirred for three hours under nitrogen at room temperature. The crude product was isolated as in Example 4 (2,3,4-trimethyl-5-carbethoxy-pyrrole) then crystallized from benzene to yield 0.55 g (73%) of colourless elongated prisms, m.p. 204°–207° C. (lit. 207° H. Fischer and W. Zerweck, Berichte 56, 523 (1923)). Anal. Calc. for $C_9H_{13}NO$: C, 71.49; H, 8.67; N, 9.26. Found: C, 71.29; H, 8.68; N, 9.38.

EXAMPLE 25

2,4,5-Trimethyl-3-carbethoxy-pyrrole

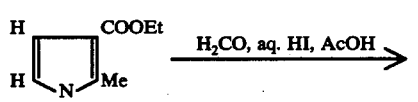

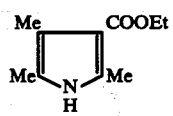

2-Methyl-3-carbethoxy-pyrrole (0.99 g), acetic acid (15 ml), aq. hydriodic acid (20 ml) and paraformaldehyde (0.78 g) were stirred for three hours at room temperature. The crude product was isolated as in Example 4 (2,3,4-trimethyl-5-carbethoxy-pyrrole) and sublimed (82° C., 4 × 10⁻³ mm) as fine colourless needles (75%), m.p. 103°–103.5° C. (lit. 104°–105° L. Knorr and K. Hess, Berichte 44, 2762 (1911)). Anal. Calc. for $C_{10}H_{15}NO_2$: C, 66.27; H, 8.34; N, 7.73. Found: C, 66.35; H, 8.17; N, 7.88.

EXAMPLE 26

5,6,7,8-Tetramethyl-1,2,3,4-tetrahydronaphthalene

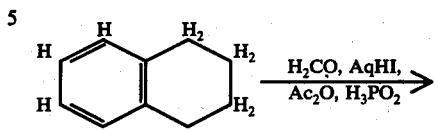

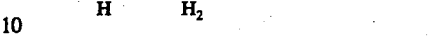

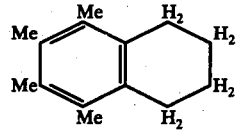

1,2,3,4-Tetrahydronaphthalene (1 ml) was added to a mixture of paraformaldehyde (2 g), aq. hydriodic acid (10 ml) and acetic anhydride (40 ml). The mixture was then stirred and heated under reflux for 4½ hr. at 90°–100° C, then at ca 116° for 5 hr. During the heating, the solution was periodically cooled to 60° and decolorized with hypophosphorous acid (total 7 ml). The warm solution was added to 125ml of water, the resulting mixture was cooled, and the crystalline crude product was separated. This was boiled for 5 min. with pyridine and the hot solution poured into boiling water (125 ml) containing 10 ml of acetic acid. The mixture was cooled and the product was separated, dried, sublimed (75° C., 1 × 10⁻⁴ mm), and extracted into 20 ml of methanol. When the solution was concentrated then allowed to cool, 925 mg of the product separated and a further 94 mg were obtained by concentrating the mother liquors. The product formed large colourless plates, m.p. 81.5°–82° C. (M. C. Kloetzel, R. P. Dayton and H. L. Herzog report 79°–79.5°. J. Am. Chem. Soc. 72, 273 (1950). Anal. Calc. for $C_{14}H_{20}$: C, 89.29, H, 10.71. Found: C, 89.43; H, 10.49.

EXAMPLE 27

Preparation of hexamethylbenzene from o-dichlorobenzene

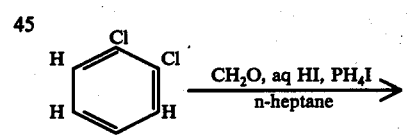

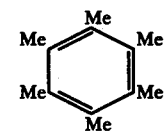

A mixture of o-dichlorobenzene (1.47 g) aq. hydriodic acid (20 ml), paraformaldehyde (2.4 g) and n-heptane (20 ml) was stirred by a "Vibro-Mischer" at 95° C (bath temp.) under reflux for 10 hours, decolorizing it periodically with phosphonium iodide. The heptane layer was then separated and washed with 20% aqueous pyridine ( 2 × 25 ml), with 10% hydrochloric acid, and with water. It was then dried and the heptane was evaporated. The residue was recrystallized from pentane as colourless crystals (621 mg, 38%). For analysis, it was sublimed (65° C., 1 × 10⁻² mm), m.p. 164°–165° C. Found: C, 88.64; H, 11.31.

EXAMPLE 28

2,3,4,5-Tetramethyl-pyrrole from 2,4-dimethyl-3-acetyl-pyrrole 2,4-Dimethyl-3-acetyl-pyrrole (1.58 g) in 25 ml of acetic acid was added in five portions during one hour to a stirred mixture of paraformaldehyde (2.07 g), aq. hydriodic acid (25 ml) and hypophosphorous acid (3 ml) maintained at 115° C. under nitrogen. The mixture was heated at 115° C. for a further 3 hours, and the crude product then isolated as in Example 4 above. Distillation (65° C, 10 mm) gave 996 mg (68%) of colourless crystals, m.p. 108°–110° C. Found: C, 77.74; H, 10.59; N, 11.19.

EXAMPLE 29

Tetramethyl-pyrrole from 2,4-dimethyl-pyrrole

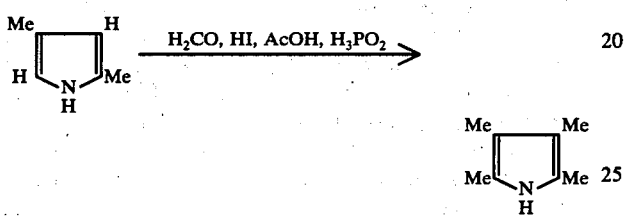

2,4-Dimethyl-pyrrole (2.06 g) in acetic acid (50 ml) was added over 2 h. to a stirred solution of paraformaldehyde (5.21 g) in hydriodic acid (75 ml), acetic acid (25 ml) and hypophosphorous acid (6 ml) at 105° C under nitrogen. The solution was heated 4 h. longer then brought to pH 9 with ammonium hydroxide at 0° C. Isolated as in Example 5 and washed with a little pentane, the colourless product (0.996 g, 37%) melted at 107°–109° C. The analytical sample, m.p. 109°–111° C, had been redistilled (60°, 8 mm), Anal. Found: C, 77.94; H, 10.56; N, 11.21.

EXAMPLE 30

2,4-Dimethyl-3-acetyl-5-isobutyl-pyrrole a. 2,4-Dimethyl-3-acetyl-pyrrole (548 mg) was dissolved in hydriodic acid (10 ml) acetic anhydride (10 ml) and hypophosphorous acid (2 ml). Isobutyraldehyde (0.75 ml) was added and the solution was stirred for 35 min. No precipitate formed. Water precipitated a yellow iodine complex (864 mg), m.p. unsharp from 90°, Beilstein test for halogen positive. This was converted into the desired product by dissolving it in ethanol and adding ammonium hydroxide. For analysis it was recrystallized from aqueous ethanol, m.p. 152° after changing to smaller crystals at 125°. Anal. Calc. for $C_{12}H_{19}NO$: C, 74.57; H, 9.91; N, 7.25. Found: C, 74.40; H, 9.73; N, 7.43.

b. When the above reaction was run in the presence of a little added phosphonium iodide, the colour faded within 1 min. and after 5 min. water precipitated the colourless product (0.7 g, 91%). It melted at 150°–152° (phase change at 125°) after being recrystallized from ethanol.

EXAMPLE 31

2-Methyl-4,5-diethyl-3carbethoxy-pyrrole

A solution of 612 mg of 2-methyl-3-carbethoxy-pyrrole in 10 ml of hydriodic acid, 10 ml of acetic anhydride and 2 ml of hypophosphorous acid was stirred while 0.35 ml of paraldehyde was dropped in. Stirring was contined for ½ h and the solution was then poured into water. For analysis, the pale yellow micro crystals which separated (0.45 g, 53%, m.p. 104°–106°) were recrystallized from aqueous ethanol. Anal Calc. for $C_{12}H_{19}NO_2$: C, 68.86; H, 9.15; N, 6.67. Found: C, 68.73; H, 9.09; N, 6.85.

EXAMPLE 32

The preparation of 2,3,4-trimethyl-5-carbethoxy-pyrrole

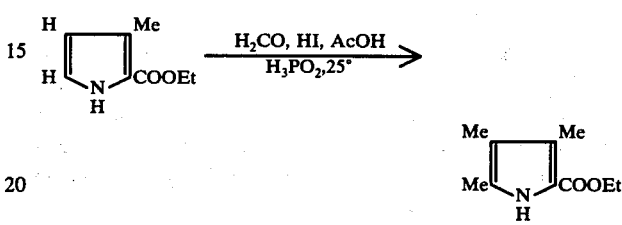

A solution of 2-carbethoxy-3-methyl-pyrrole [1] (0.306 g, 2 millimols) and paraformaldehyde (0.3 g) in acetic acid (5 ml) hydriodic acid (5 ml) and hypophosphorous acid (1 ml) was stirred for 2½ hrs at 25° then poured into water. The mixture was made alkyline with ammonium hydroxide and the product then separated, dried and recrystallized from ether-n-pentane as colourless needles (0.121 g); 33%), m.p. 127°–129° (lit[2] m.p. 128°). Anal Calc. for $C_{10}H_{15}NO_2$: C, 66.27; H, 8.34; N, 7.73. Found: C, 66.09; H, 8.19; N, 7.79.

[1] A. H. Corwin and J. L. Straughn, J. Amer. Chem. Soc., 70, 1416 (1948)
[2] H. Fischer and H. Orth, "Chemie des Pyrols", Vol. 1, p. 239, Akademische, Leipzig 1934.

EXAMPLE 33

The preparation of 2,3,4-trimethyl-5-carbethoxy-pyrrole

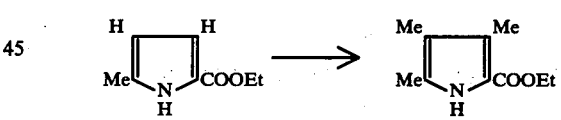

As in Example 32 but using 2-methyl-5-carbethoxy-pyrrole [3]. It formed colourless needles (50%), m.p. 127°–129°. Anal. Found: C, 66.42; H, 8.40; N, 7.89.

[3] H. Fischer and H. Orth. loc. cit. p. 238.

EXAMPLE 34

The preparation of 2,3,4-trimethyl-5-carbethoxy-pyrrole

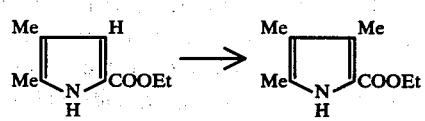

As in Example 32 but using 2,3-dimethyl-5-carbethoxy-pyrrole [4]. It formed colourless needles (72%), m.p. 127°–129°. Anal. Found: C, 66.13; H, 8.41; N, 7.71.

[4] H. Fischer and H. Orth. loc. cit. p. 238.

EXAMPLE 35

The preparation of 2,3,4-trimethyl-5-carbethoxy-pyrrole

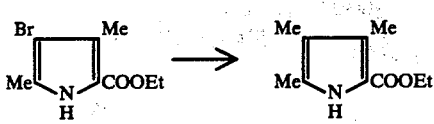

As in Example 32 but using 2,4-dimethyl-3-bromo-5-carbethoxy-pyrrole[5]. It formed colourless needles (60%), m.p. 126°–127°. Anal. Found: C, 66.20; H, 8.30; N, 7.88.

[5] H. Fischer and H. Orth. loc. cit. p. 92.

EXAMPLE 36

The preparation of 2,4-dimethyl-3-ethyl-5-carbethoxy-pyrrole

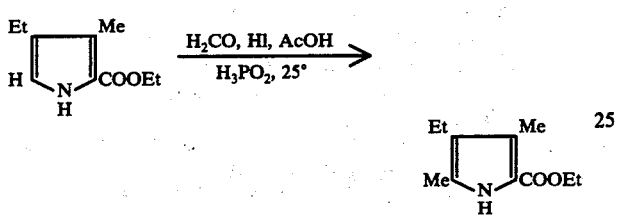

As in Example 32 but using 3-ethyl-4-methyl-5-carbethoxy-pyrrole[6]. It formed colourless prisms (53%), m.p. 91°–92°, 89°–90° when mixed with authentic material of m.p. 89°–90°[7]. Anal Calc. for $C_{11}H_{17}NO_2$: C, 67.66; H, 8.78; N, 7.17. Found: C, 67.69; H, 8.72; N, 7.19.

[6] H. Fischer and H. Orth, loc, cit., p. 241.
[7] F. K. Sinaigo and H. Adkins, J. Amer. Chem. Soc., 58, 709 (1936).

EXAMPLE 37

The preparation of 2,3-diethyl-4-methyl-5-carbethoxy-pyrrole

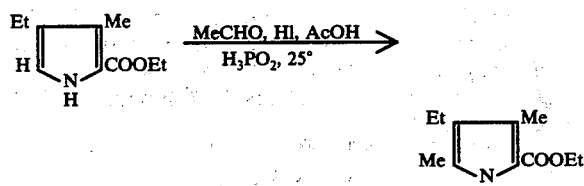

As in Example 32 but using 3-ethyl-4-methyl-5-carbethoxy-pyrrole and paraldehyde. Colourless prisms (64%), m.p. 71°–73° (lit. [8] 73°–74°). Anal. Calc. for $C_{12}H_{19}NO_2$: C, 68.86; H, 9.15; N, 6.67. Found: C, 68.71; H, 9.11; N, 6.84.

[8] S. F. MacDonald and A. Markovac, Canad. J. Chem., 43, 3247 (1965).

EXAMPLE 38

2,4,5-Trimethyl-3-carbethoxy-pyrrole

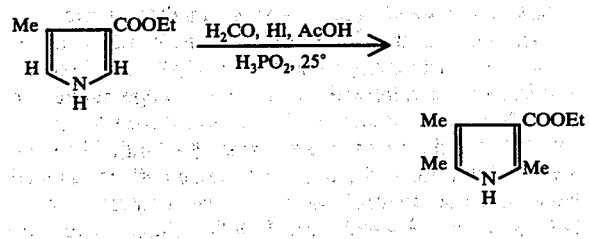

As in Example 32 but using 3-methyl-4-carbethoxy-pyrrole[9]. The product (70%) formed colourless needles, m.p. 103°–105° unchanged on admixture with the product of Example 39 below.

[9] H. Fischer and H. Orth, loc. cit. p. 246.

EXAMPLE 39

2,4,5-Trimethyl-3-carbethoxy-pyrrole

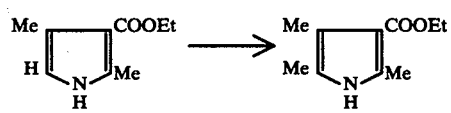

As in Example 32 but using 2,4-dimethyl-3-carbethoxy-pyrrole[10]. It formed colourless needles (67%), m.p. 102°–104° (lit[11] 104°–105°). Anal. Found: C, 66.12; H, 8.46; N, 7.85.

[10] H. Fischer and H. Orth, loc. cit., p. 247.
[11] H. Fischer and H. Orth, loc. cit., p. 248.

EXAMPLE 40

2,4,5-Trimethyl-3-carbethoxy-pyrrole

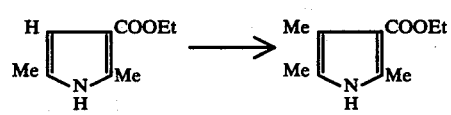

As in Example 32 but using 2,5-dimethyl-3-carbethoxy-pyrrole[12]. Colourless needles (70%), m.p. 103°–105°. Anal. Found: C, 66.10; H, 8.30; N, 7.81.

[12] H. Fischer and H. Orth, loc. cit., p. 247.

EXAMPLE 41

2,4-Dimethyl-3,5-dicarbethoxy-pyrrole

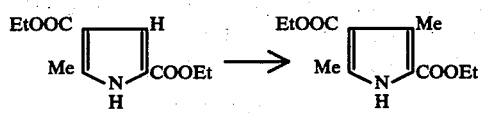

As in Example 32 but using 2-methyl-3,5-dicarbethoxy-pyrrole[13] and stirring for ½ hr then pouring the mixture (containing an insoluble labile complex of the product with iodine) into water. Colourless needles (70%), m.p. 135° (lit[14] 136°) from methanol. Anal. Calc. for $C_{12}H_{17}NO_4$: C, 60.24; H, 7.16; N, 5.85. Found: C, 60.16, H, 7.10; N, 5.80.

[13] H. Fischer and H. Orth, loc. cit., p. 255.
[14] H. Fischer and H. Orth, loc. cit., p. 255.

EXAMPLE 42

3,4-Dimethyl-2,5-dicarbethoxy-pyrrole

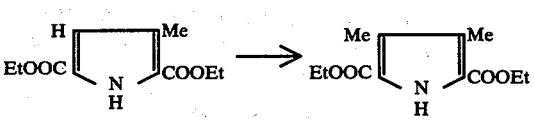

As in Example 32 but using 3-methyl-2,5-dicarbethoxy-pyrrole[15] and stirring at 45° for 3 hrs to redissolve a compound containing iodine which precipitated. It formed colourless crystals (45%) from n-pentane, m.p. 66°–68°. Anal Calc. for $C_{12}H_{17}NO_4$: C, 60.24; H, 7.16; N, 5.85. Found: C, 59.93; H, 7.21; N, 6.06.

[15] A. H. Corwin and J. L. Straughn, loc. cit.,

EXAMPLE 43

2,3-Dimethyl-4-ethyl-5-carbethoxy-pyrrole

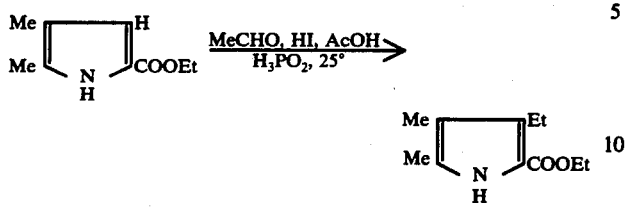

As in Example 32 but using 2,3-dimethyl-5-carbethoxy-pyrrole and paraldehyde. Colourless prisms (51%), m.p. 95°–97° (lit[16] m.p. 97°). Anal. Calc. for $C_{11}H_{17}NO_2$: C, 67.66; H, 8.78; N, 7.17. Found: C, 67.59; H, 8.49; N, 7.23.

[16] H. Fischer and H. Orth, loc. cit., p. 242.

EXAMPLE 44

2,3-Dimethyl-4-isobutyl-5-carbethoxy-pyrrole

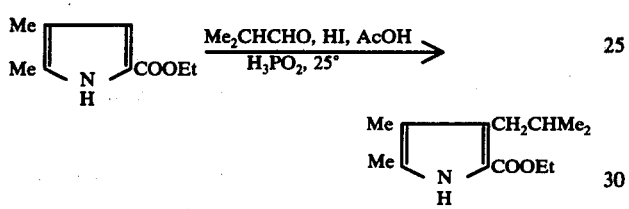

As in Example 32 but using 2,3-dimethyl-5-carbethoxy-pyrrole and isobutyraldehyde, pouring the mixture into water after 3 hrs and extracting the product from the alkaline mixture with ether. It was distilled (70°, 1 × 10⁻⁴ mm) and crystallized from pentane as colourless prisms (45%), m.p. 109°–111°. Anal. Calc. for $C_{13}H_{21}NO_2$: C, 69.92; H, 9.48; N, 6.27. Found: C, 70.23; H, 9.79; N, 6.27.

EXAMPLE 45

2,3-Dimethyl-4-n-heptyl-5-carbethoxy-pyrrole

Obtained as in Example 44 using 2,3-dimethyl-5-carbethoxy-pyrrole and n-heptaldehyde, the product (b.p. 100°, 1 × 10⁻³ mm) formed colourless crystals (47%) from pentane, m.p. 68°–69°. Anal. Calc. for $C_{16}H_{27}NO_2$: C, 72.41, H, 10.26; N, 5.28. Found: C, 72.23; H, 10.27; N, 5.15.

EXAMPLE 46

2,3-Dimethyl-4-n-dodecyl-5-carbethoxy-pyrrole

As in Example 32 but using 2,3-dimethyl-5-carbethoxy-pyrrole and laurylaldehyde and stirring for 3 hrs. It formed colourless prisms (35%), m.p. 70°–71°. Anal. Calc. for $C_{21}H_{37}NO_2$: C, 75.17; H, 11.12; N, 4.18. Found: C, 75.08; H, 11.04; N, 4.30.

EXAMPLE 47

2,3-Dimethyl-4-n-octadecyl-5-carbethoxy-pyrrole

Obtained as in Example 44 using 2,3-dimethyl-5-carbethoxy-pyrrole and the trimer of stearaldehyde. The product (b.p. 145°–150°, 1 × 10⁻⁴ mm) formed colourless crystals (30%) from ether-n-pentane, m.p. 78°–80°. Anal Calc. for $C_{27}H_{49}NO_2$: C, 77.27; H, 11.77; N, 3.34. Found: C, 77.17; H, 11.68; N, 3.42.

EXAMPLE 48

2,4-Dimethyl-5-ethyl-3-carbethoxy-pyrrole

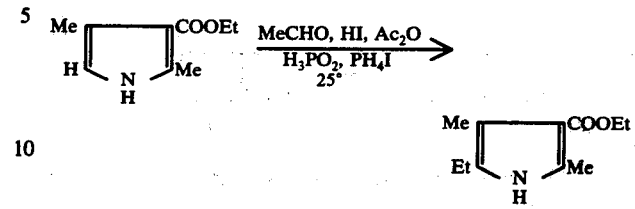

2,4-Dimethyl-3-carbethoxy-pyrrole (0.668 g) was dissolved in a mixture of hydriodic acid (10 ml), acetic anhydride (10 ml) and hypophosphorous acid (2 ml). Paraldehyde (0.75 ml) was added. The solution was stirred 5 min., decolorized with phosphonium iodide, and poured into ice water. The cooled mixture was brought to pH 8 with ammonium hydroxide. The product was filtered off and distilled (90°–100°, 5 × 10⁻⁴ mm), giving colourless crystals (53%), m.p. 108°–109° after changing to prisms at 105°. For analysis, it was recrystallized from hexane as prismatic rods, m.p. 107°–109° (lit[17] 106°–107°).

Anal. Calc. for $C_{11}H_{17}NO_2$: C, 67.66; H, 8.78; N, 7.17. Found: C, 67.31; H, 8.72; N, 7.08.

[17] L. Knorr and K. Hess, Chem. Ber., 44, 2762 (1911); 45 2626, (1912), Note 1.

EXAMPLE 49

2,5-Dimethyl-3-ethyl-4-carbethoxy-pyrrole

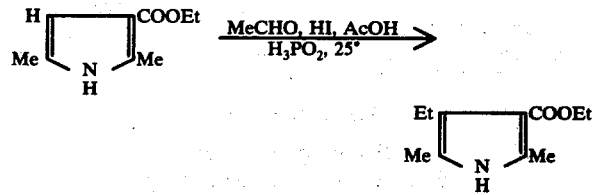

As in Example 32 but using 2,5-dimethyl-3-carbethoxy-pyrrole and paraldehyde. Colourless crystals (75%), m.p. 105°–107° (lit[18] 106°–107°). Anal. Calc. for $C_{11}H_{17}NO_2$: C, 67.66; H, 8.78; N, 7.17. Found: C, 67.54; H, 8.69; N, 7.28.

[18] E. Vecchi, Gazz. chim. ital., 44, I, 473 (1914).

EXAMPLE 50

2,4-Dimethyl-3-n-propyl-5-carbethoxy-pyrrole

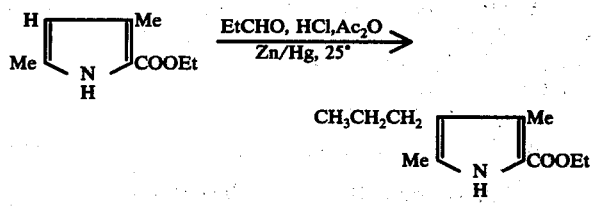

Acetic anhydride (20 ml) was added to stirred and cooled concentrated hydrochloric acid (5 ml), and 2,4-dimethyl-5-carbethoxy-pyrrole (0.668 g) was dissolved in this. Propionaldehyde (0.6 ml) and amalgamated zinc (10 g, 20 mesh) was added, the mixture stirred 15 min, at 20°–25° then decanted into ice water (100 ml). The solid was distilled (80°–95°, 1 × 10⁻⁴ mm) and crystallized from aqueous ethanol as colourless irregular prisms (48%), m.p. 99°–99.5° (lit[19] 98°). Anal. Calc. for $C_{12}H_{19}NO_2$: C, 68.86; H, 9.15; N, 6.69. Found: C, 68.75; H, 9.19; N, 6.89.

[19] H. Fischer, M. Goldschmidt and W. Nussler, Annalen, 486, 34 (1931).

EXAMPLE 51

2,4-Dimethyl-3-isopropyl-5-carbethoxy-pyrrole

As Example 50 but using acetone. The colourless crude product (50%), m.p. 105°–108° after changing to hexagonal plates, was purified in the same way to give irregular plates, m.p. 105°–106.5°. Anal. Calc. for $C_{12}H_{19}NO_2$: C, 68.86; H, 9.15; N, 6.69. Found: C, 68.70; H, 8.98; N, 6.79.

EXAMPLE 52

2,4-Dimethyl-3-n-butyl-5-carbethoxy-pyrrole

As Example 50 but using n-butyraldehyde. The colourless crude product (75%), m.p. 99°–103°, was distilled (to 115°, 1 × $10^{-5}$ mm) and crystallized from aqueous ethanol as colourless plates, m.p. 101°–103°. Anal. Calc. for $C_{13}H_{21}NO_2$: C, 69.92; H, 9.48; N, 6.27. Found: C, 69.84; H, 9.37; N, 6.37.

EXAMPLE 53

2,4-Dimethyl-3-n-heptyl-5-carbethoxy-pyrrole

As Example 50 but using n-heptaldehyde. After pouring the mixture into water, the product was extracted with ether and distilled (100°, 1 × $10^{-4}$ mm) to give colourless crystals, m.p. 47°–49°. Anal. Calc. for $C_{16}H_{27}NO_2$: C, 72.41; H, 10.26; N, 5.28. Found: C, 72.60; H, 10.11; N, 5.23.

EXAMPLE 54

2,4-Dimethyl-3-n-dodecyl-5-carbethoxy-pyrrole

As Example 50 but using lauraldehyde, stirring for 1 hr. at 25°–30° and pouring the solution into water (100 ml) containing ammonium hydroxide (5 ml) and Girrard's reagent "T" (2 g). After two distillations (130°, 1 × $10^{-4}$ mm) it formed colourless crystals (27%), m.p. 65°–67°. Anal. Calc. for $C_{21}H_{37}NO_2$: C, 75.17; H, 11.12; N, 4.18. Found: C, 74.95; H, 11.01; N, 4.24.

EXAMPLE 55

2,4-Dimethyl-3-n-octadecyl-5-carbethoxy-pyrrole

As Example 50 but using stearaldehyde trimer and stirring for 3 hr. at 25°. The solution was poured into water and the mixture made alkaline with ammonia. The product was extracted with ether, distilled (145°–150° 1 × $10^{-4}$ mm) and crystallized from ether-pentane as colourless crystals (30%), m.p. 76°–78°. Anal. Calc. for $C_{27}H_{49}NO_2$: C, 77.27; H, 11.77; N, 3.34. Found: C, 77.11; H, 11.71; N, 3.27.

EXAMPLE 56

2,4-Dimethyl-3-acetyl-5-cyclopentyl-pyrrole

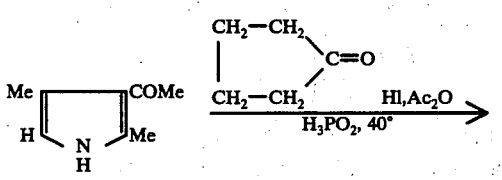

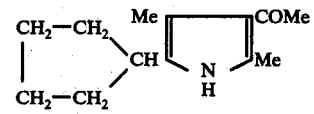

2,4-Dimethyl-3-acetyl-pyrrole (0.548 g) was dissolved in a mixture of hydriodic acid (10 ml), acetic anhydride (10 ml) and hypophosphorous acid (2 ml). The solution was stirred at 40° while cyclopentanone (1.5 ml) was added in three portions over ¾ hr. After stirring an additional ½ hr., the solution was poured into ice water (125 ml) and the pale yellow product (95%), m.p. 161.5°–163.5° after changing to prisms at ca 140°, separated. For analysis it was recrystallized successively from hexane, from aqueous methanol and again from n-hexane as pale pink prisms m.p. 167.5°–168° (lit[20], 164.5°–165.5°). Anal. Calc. for $C_{13}H_{19}NO$: C, 76.05, H, 9.33; N, 6.82. Found: C, 76.12; H, 9.21; N, 6.65.

[20] Endo Laboratories Inc. (by K. Schoen and I. J. Pachter). Belg. Pat. 670, 796, Jan. 31, 1966; cf. C.A. 65, 16943 (1966).

EXAMPLE 57

2,4-Dimethyl-3-acetyl-5-(2-amino-ethyl)-pyrrole

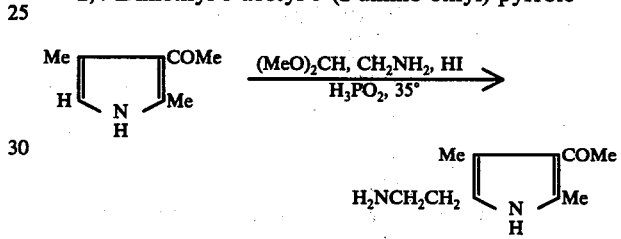

Aminoacetaldehyde dimethyl acetal (0.75 ml) was added to a stirred solution of 2,4-dimethyl-3-acetyl-pyrrole (0.548 g) in 10 ml of hydriodic acid and 2 ml of hypophosphorous acid. The solution was stirred for 4 hr. at 35° then evaporated in a shallow dish in a vacuum disiccator, finally at 0.1 mm, and the residue twice slurried and filtered with acetone. The clarified solution of the solid in water (5 ml) was made strongly alkaline with KOH, saturated with potassium carbonate, and extracted repeatedly with ether. The ether solution (125 ml) was concentrated, adding n-pentane toward the end, to precipitate the product (29%) as pale yellow prisms, m.p. 106.5°–107.5°. Anal. Calc. for $C_{10}H_{16}N_2O$: C, 66.63; H, 8.95; N, 15.54; neut. equiv. 180. Found: C, 66.51; H, 8.89; N, 15.62; neut. equiv. 182.

EXAMPLE 58

Tetramethyl-pyrrole

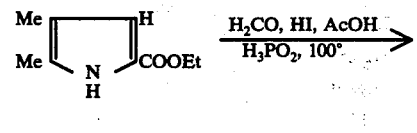

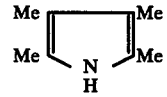

A solution of 2,3-dimethyl-5-carbethoxy-pyrrole (0.82 g) in acetic acid (10 ml), hydriodic acid (10 ml), hypophosphorous acid (2 ml) and paraformaldehyde (0.6 g) was stirred and heated at 100° under nitrogen for 3 hr. then poured into water. The mixture was made alkaline with ammonia and extracted with ether. The ether was evaporated and the residue distilled (65°, 15 mm) to give the product (53%) m.p. 105°–107°.

EXAMPLE 59

Tetramethyl-pyrrole

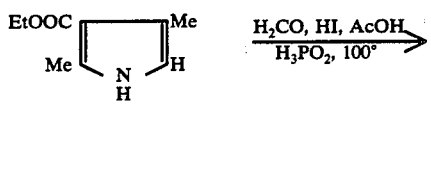

As in Example 58 using 2,4-dimethyl-3-carbethoxy-pyrrole to obtain 0.32 g (53%), m.p. 105°–107°. Anal. Calc. for $C_8H_{13}N$: C, 77.99; H, 10.64; N, 11.37. Found: C, 77.96; H, 10.43; N, 11.47.

EXAMPLE 60

Tetramethyl-pyrrole

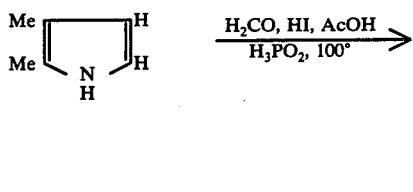

As in Example 58, using 2,3-dimethyl-pyrrole (2 g), acetic acid (50 ml), hydriodic acid (50 ml), hypophosphorous acid (5 ml) and paraformaldehyde (1.2 g). Yield 51%, m.p. 105°–107°. Anal. Found: C, 77.81; H, 10.32; N, 11.45.

EXAMPLE 61

Tetramethyl-pyrrole

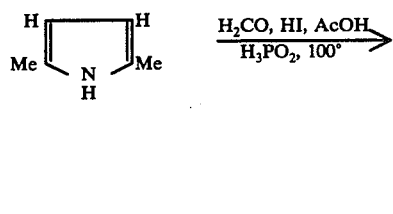

As in Example 60, using 2,5-dimethyl-pyrrole. Yield 49%, m.p. 105°–107°.

EXAMPLE 62

2,3-Dimethyl-4,5-diethyl-pyrrole

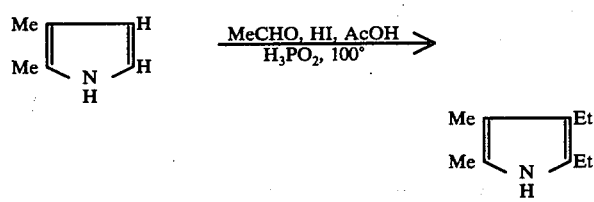

As in Example 58, using 2,3-dimethyl-pyrrole (1.6 g), acetic acid (40 ml), hydriodic acid (40 ml), hypophosphorous acid (8 ml) and paraldehyde (1.4 ml). The product (48%) was an oil, b.p. 45°–47° (0.05 mm). Anal.

Calc. for $C_{10}H_{17}N$: C, 79.40; H, 11.34; N, 9.26. Found: C, 79.09; H, 11.27; N, 9.37.

EXAMPLE 63

2,5-Dimethyl-3,4-diethyl-pyrrole [21]

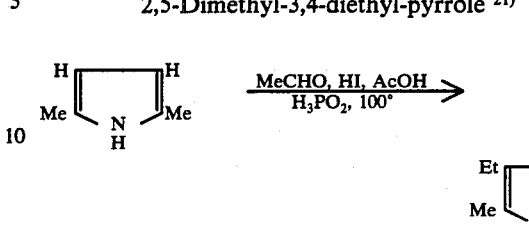

As in Example 58, using 2,5-dimethyl-pyrrole (2g), acetic acid (50 ml), hydriodic acid (50 ml), hypophosphorous acid (10 ml) and paraldehyde (1.4 ml). The product (46%) was an oil, b.p. 48°–50° (0.05 mm). Anal. Calc. for $C_{10}H_{17}N$: C, 79.40; H, 11.34; N, 9.26. Found: C, 79.21; H, 11.53; N, 9.09.

[21] cf. H. Fischer and H. Orth, loc. cit., p. 58.

EXAMPLE 64

2,4-Dimethyl-3,5-diethyl-pyrrole[22]

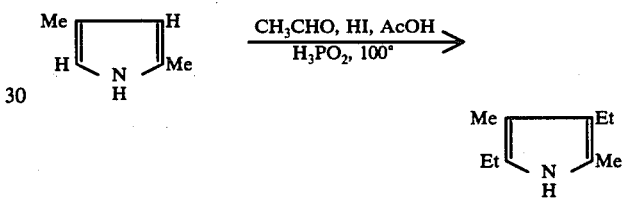

As in Example 62, using 2,4-dimethyl-pyrrole. The product was an oil (56%), b.p. 50°–52° (0.06 mm). Anal. Calc. for $C_{10}H_{17}N$: C, 79.40; H, 11.34; N, 9.26. Found: C, 79.22; H, 11.19; N, 9.44.

[22] cf. H. Fischer and H. Orth. loc. cit., p. 58; F. K. Sinaigo and H. Adkins, loc. cit.

EXAMPLE 65

2,3-Dimethyl-5-carboxy-pyrrole-4-propionic acid Diethyl Ester

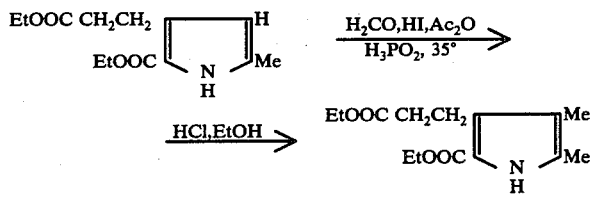

2-Methyl-5-carboxy-pyrrole-4-propionic acid diethyl ester[23] (506 mg) was dissolved in hydriodic acid (5 ml), acetic anhydride (5 ml) and hypophosphorous acid (1 ml). Paraformaldehyde (120 mg) was added, and the mixture was stirred for 25 min. then evaporated (rotary evaporator, 25° then 35° bath, finally 0.5 mm). The residue was rubbed with 2 ml of water then left at 0° overnight. The solid was separated, dried and re-esterified by warming to solution in 6% hydrogen chloride in ethanol (3 ml). The solution, after standing at 20° then at 0°, was scratched. The product which separated was recrystallized from pentane (thimble) as colourless plates (48%), m.p. 90.5°–91.5° unchanged when mixed with authentic material [24]. Anal. Calc. for $C_{14}H_{21}O_4N$:

C, 62.90, H, 7.92; N, 5.24. Found: C, 63.06; H, 8.03; N, 5.19.

[23] S. F. MacDonald, J. Chem. Soc., 4176 (1952).
[24] F. Morsingh and S. F. MacDonald, J. Amer. Chem. Soc., 82, 4377 (1960).

EXAMPLE 66

2-Methyl-5-carboxy-pyrrole-3-acetic acid-4-propionic acid Triethyl Ester

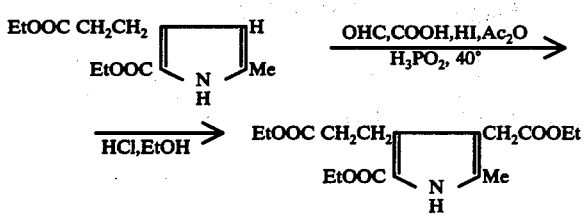

2-Methyl-5-carboxy-pyrrole-4-propionic acid diethyl ester (1.012 g) was dissolved in hydriodic acid (10 ml), acetic anhydride (10 ml) and hypophosphorous acid (2 ml). This solution was stirred at 40° while adding 1.1 g glyoxylic acid monohydrate in 3 portions over 15 min. It was stirred 15 min. more then evaporated (rotary, 25° then 35° bath, finally 0.5 mm). The residue was rubbed with 4 ml of water and left at 0° overnight. The solid was separated, washed with water (2 ml) and dried. It was warmed to solution in 5 ml of 7% hydrogen chloride in ethanol, left 6 hr. at 20° then at 0°. The product which crystallized, together with that from the concentrated and cooled mother liquor, was recrystallized from pentane (thimble) as long colourless needles (1.022 g, 75%), m.p. 66°-66.5°, undepressed when mixed with authentic material[25]. Anal. Calc. for $C_{17}H_{25}NO_6$: C, 60.16; H, 7.43; N, 4.13. Found: C, 60.40; H, 7.65; N, 4.31.
[25] S. F. MacDonald and R. J. Stedman, Canad. J. Chem., 33, 458 (1955)

EXAMPLE 67

Fluorene from 2-biphenyl-carboxaldehyde diethyl acetal

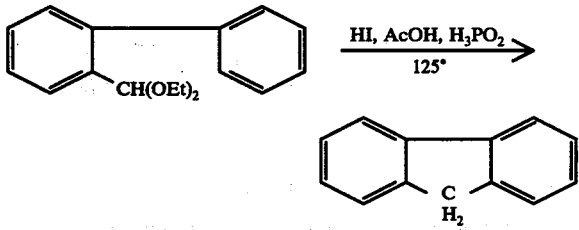

Hydriodic acid (10 ml) and hypophosphorous acid (1 ml) were heated and stirred at ca. 100° while 1.024 g of 2-biphenyl-carboxaldehyde diethyl acetal (m.p. 63°, obtained from 2-biphenyl-magnesium iodide and ethyl orthoformate, biphenyl being removed from the crude product by draining in tile then steam-distillation. Anal. Calc. for $C_{17}H_{20}O_2$: C, 79.65; H, 7.86. Found: C, 79.48; H, 7.84) in 5 ml of acetic acid was added. The mixture was stirred and slowly distilled under the vapour reached 125° after 1 hr. The combined distillate and residue were diluted with water and the product isolated using ether. It was sublimed at <100° (5 × $10^{-4}$ mm) and crystallized from methanol as colourless prisms (83%, m.p. 117.5°-118°, mixed m.p. with authentic fluorene of m.p. 118°-119°:117.5°-119°). Anal. Calcd. for $C_{13}H_{10}$: C, 93.94; H, 6.06. Found: C, 93.67; H, 6.20.

It will be seen from the above example that an inter molecular reaction takes place, both the alkylatable compound and the carbonyl compound being different groups in the same molecule with the result that ring closure is effected.

In the aforesaid Examples:

The hypophosphorous acid used was 50%. The hydriodic acid was stored at 0° over phosphonium iodide.

The hydriodic acid-acetic anhydride mixture was best made by adding the acetic anhydride slowly to the hydriodic acid, cooled with water and stirred magnetically, then adding the hypophosphorous acid; otherwise, a yellow solid might form.

The phosphonium iodide was prepared as follows: hydriodic acid (D = 1.95, 115 ml) and red phosphorous (50 g) were stirred magnetically in a 250 ml flask, surmounted by a 6 inch air condenser under a reflux condenser and heated by an oil bath. The bath temperature was slowly raised to 80° held at that temperature for 1½ hr., then slowly raised to 105°. The phosphonium iodide was periodically removed from the air condenser and stored at 0° under hydriodic acid (D 1.95). Yield 74 gm; and the reactant 2,4-dimethyl-3-acetyl-pyrrole was prepared as follows, 2,4-dimethyl-3-acetyl-5-carbethoxy-pyrrole (8 g) and 40 ml of 10% aqueous sodium hydroxide were heated for 4 h at 175° in a "Teflon" (Trademark of DuPont for polytetrafluoroethylene) lined brass tube. The contents of the tube were ground up and filtered. The solid was washed with water and distilled (125°, 1 × $10^{-3}$ mm) to give a colourless product (4.72 g, 90%), m.p. 140°-140.5° (lit 137°, H. Fischer and H. Orth. "Chemie des Pyrrols", Leipzig 1934, I, p. 185). Anal. Calc. for $C_8H_{11}N$: C, 70.04; H, 8.08; N, 10.21. Found: C, 70.22; H, 8.21; N, 9.99.

The 2,4-dimethyl-3-acetyl-5-ethyl-pyrrole of Example 20 has been prepared by F. K. Sinaigo and H. Adkins, J.A.C.S. 58, 709 and is given a m.p. of 157-158. The products of Examples 7, 8, 22, 24, 30 and 56 are known compounds disclosed in Belgian Pat. No. 670,796 issued Jan. 31, 1966.

The products of Examples 4, 14, 34, 43 to 47, 50 to 55, 65 and 66 are useful for synthetic and analytic work on natural pigments.

EXAMPLE 68

2-Carbethoxy-3-n-propyl-4,5-dimethylpyrrole

Hydriodic acid (d 1.95, 10 ml) was slowly added to 10 ml of stirred and cooled acetic acid; hypophosphorous acid (50%, 2 ml) was then added. 2-Carbethoxy-4,5-dimethylpyrrole (0.004 mol) was added to the mixture at room temperature followed by propionaldehyde (0.008 mol). The solution was stirred 2½ h at ca. 25° C. then poured into 200 ml of water. This was made alkaline with ammonia, extracted with ether, and the ether was evaporated to leave the crude product. This was an oil which solidified after distillation (1 × $10^{-4}$ mm). It was recrystallized from aqueous ethanol, then from ethanol m.p. 101°-104° C. (lit. 102° C), yield 40%.

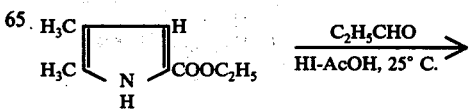

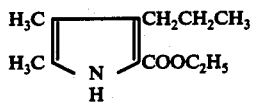

EXAMPLE 69

2,5-Diethyl-4-methyl-3-carbethoxypyrrole

The procedure of Example 68 was followed but using 2,5-diethyl-3-carbethoxypyrrole and paraformaldehyde. The product obtained was 2,5-diethyl-4-methyl-3-carbethoxypyrrole mp and mixed mp 101°–103° C (lit. 101° to 103° C).

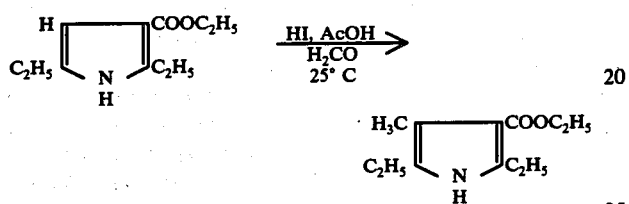

EXAMPLE 70

2-Carbethoxy-3-n-propyl-4-methyl-5-ethylpyrrole

The crude product, obtained as in Example 68 but using 2-carbethoxy-4-methyl-5-ethylpyrrole was an oil which largely solidified after distillation (75° C. 1 × $10^{-4}$ mm). It was dried on tile then crystallized from ethanol as long colorless needles (19%), m.p. 73°–74° C.

Anal. Calcd. for $C_{13}H_{21}O_2N$: C, 69.91; H, 9.48; N, 6.27. Found: C, 69.77; H, 9.32; N, 6.42.

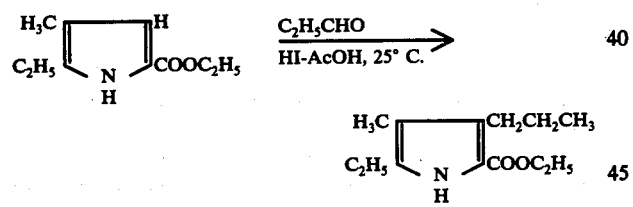

EXAMPLE 71

2-Carbethoxy-3-i-butyl-4-methyl-5-ethylpyrrole

The crude product, obtained in Example 68 but using 2-carbethoxy-4-methyl-5-ethylpyrrole and isobutyraldehyde, solidified at 0° C. after distillation (70° C. 1 × $10^{-4}$mm). It was recrystallized twice from methanol, m.p. 53°–55° C. (12%).

Anal. Calcd. for $C_{14}H_{23}O_2N$: C, 70.85; H, 9.77; N, 5.90. Found: C, 70.83; H, 9.86; N, 6.06.

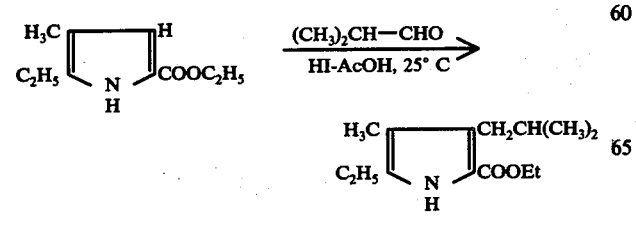

EXAMPLE 72

2-Carbethoxy-3-ethyl-4-methyl-5-n-propylpyrrole

The crude product, obtained in Example 68 but using 2-carbethoxy-4-methyl-5-n-propylpyrrole and paraldehyde, was crystallized from aqueous ethanol, sublimed, recrystallized and resublimed, m.p. 58°–59.5° C.

Anal. Calcd. for $C_{13}H_{21}O_2N$: C, 69.92; H, 9.48; N, 6.27. Found: C, 69.75; H, 9.50; N, 6.45.

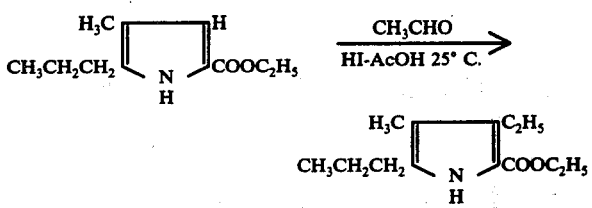

EXAMPLE 73

2-n-Propyl-3-(2-carbethoxy-ethyl)-4-methyl-5-carbethoxypyrrole 3-(2-Carbethoxy-ethyl)-4-methyl-5-carbethoxypyrrole (0.4 g (35)), 5ml of hydriodic acid, 5 ml of acetic acid, 1 ml of hypophosphorous acid and 0.23 ml of propionaldehyde were reacted as above. The solution was poured into 60 ml of water which was then brought to pH 5 with ammonia. The precipitate (of the partially hydrolyzed product) was esterified in 5 ml of 5% ethanolic HCl. The solvent was evaporated and the residue was distilled then recrystallized from pentane (0.1 g), m.p. 61.5°–63.5° C (lit. 63° – 64° C.).

Anal. Calcd. for $C_{16}H_{25}O_4N$: C, 65.08; H, 8.53; N, 4.74. Found: C, 65.19; H, 8.40; N, 4.90.

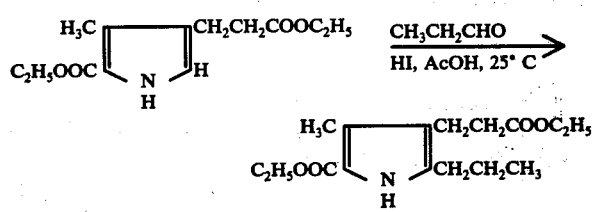

EXAMPLE 74

2-Methyl-3,4-diethyl-5-carbethoxypyrrole

Acetic anhydride (20 ml) was stirred into 5 ml of concentrated hydrochloric acid with cooling. 2-Methyl-4-ethyl-5-carbethoxypyrrole (0.004 mol), paraldehyde (0.008 mol), and zinc amalgam (20 mesh, 10 g) were added at 25° C. and the mixture was stirred ¼ h. The solution was decanted into 200 ml of water, this was made alkaline with ammonia and the crude product was filtered off. It was purified by sublimation, m.p. 76°–77° C. (lit. 75° C.). Yield 20%.

Anal. Calcd. for $C_{12}H_{19}O_2N$: C, 68.86; H, 8.96; N, 6.67. Found: C, 68.83; H, 9.15; N, 6.87.

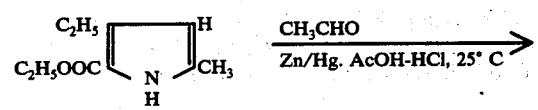

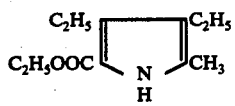

EXAMPLE 75

2-Ethyl-3-n-propyl-4-methyl-5-carbethoxypyrrole

The crude product, obtained as in Example 74 but using 2-ethyl-4-methyl-5-carbethoxypyrrole and propionaldehyde, was sublimed (80° C. 1 × 10⁻⁴ mm), m.p. 86°-87° C. (50%).

Anal. Calcd. for $C_{13}H_{21}O_2N$: C, 69.92; H, 9.48; N, 6.27. Found: C, 70.14; H, 9.31; N, 6.48.

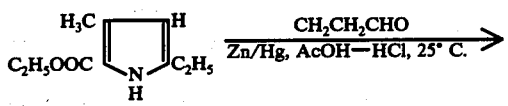

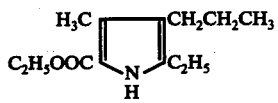

EXAMPLE 76

2-Ethyl-3-i-butyl-4-methyl-5-carbethoxypyrrole

The crude product, obtained as in Example 74 but using 2-ethyl-4-methyl-5-carbethoxypyrrole and isobutyraldehyde was sublimed (80° C. 1 × 10⁻⁴ mm) and recrystallized from aqueous ethanol, m.p. 94°-96° C (44%).

Anal. Calcd. for $C_{14}H_{23}O_2N$: C, 70.85; H, 9.77; N, 5.90. Found: C, 70.95; H, 9.59; N, 6.07.

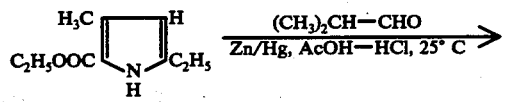

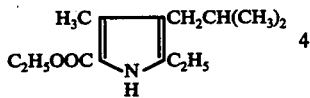

EXAMPLE 77

2,4-Di-n-propyl-3-methyl-5-carbethoxypyrrole

The crude product, obtained as in Example 74 but using 2,4-di-n-propyl-5-carbethoxypyrrole and paraformaldehyde, was extracted with ether then sublimed (65° C. 1 × 10⁻⁴ mm), m.p. 78°-80° C. (17%).

Anal. Calcd. for $C_{14}H_{23}O_2N$: C, 70.85; H, 9.77; N, 5.90. Found: C, 70.72; H, 9.74; N, 5.98.

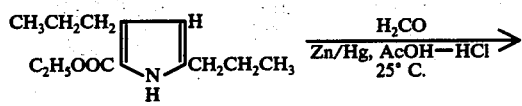

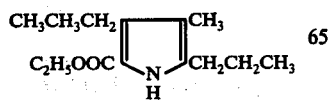

EXAMPLE 78

2,3-Di-n-propyl-4-methyl-5-carbethoxypyrrole

The crude product, obtained as in Example 74 but using 2-n-propyl-4-methyl-5-carbethoxypyrrole and propionaldehyde, was distilled (80° C 1 × 10⁻⁴ mm). The partially solidified distillate was dried on tile then recrystallized twice from aqueous ethanol as colorless needles (20%), m.p. 84°-87° C.

Anal. Calcd. for $C_{14}H_{23}O_2N$: C, 70.85; H, 9.77; N, 5.90. Found: C, 70.68; H, 9.53; N, 6.05.

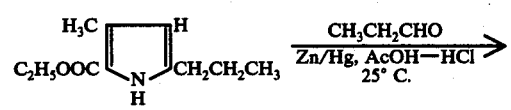

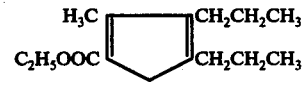

EXAMPLE 79

2-n-Propyl-3-i-butyl-4-methyl-5-carbethoxypyrrole

The crude product, obtained as in Example 74 using 2-n-propyl-4-methyl-5-carbethoxypyrrole (0.65g) and isobutyraldehyde (0.5 g), was repeatedly sublimed (65° C 1 × 10⁻⁴ mm) and recrystallized to remove starting material which was evident in the g.l.p.c gas-liquid chromatogram; yield, 30 mg, m.p. 78°-79° C.

Anal. Calcd. for $C_{15}H_{25}O_2N$: C, 71.67; H, 10.03; N, 5.57. Found: 71.49; H, 10.21; N, 5.68.

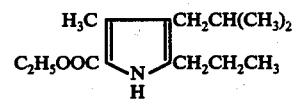

EXAMPLE 80

2,4-Dimethyl-3-sec-butyl-5-carbethoxypyrrole

The crude product, obtained as in Example 74 but using 2,4-dimethyl-5-carbethoxypyrrole with 2-butanone and stirring at 30°-35° C, was sublimed then thrice recrystallized from ethanol as colorless plates (130 mg), m.p. 102°-104° C.

Anal. Calcd. for $C_{13}H_{21}O_2N$: C, 69.92; H, 9.48; N, 6.27. Found: C, 70.08; H, 9.31; N, 6.26.

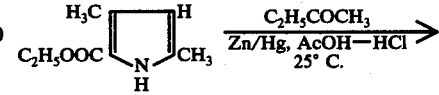

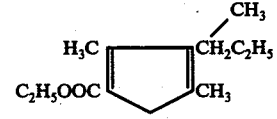

EXAMPLE 81

2,3,4-Triethyl-5-carbethoxypyrrole

The crude product, obtained as in Example 74 but using 2,4-diethyl-5-carbethoxypyrrole (5e) with paraldehyde, was this time extracted by ether. The ether was evaporated and the residue was distilled. The distillate partially solidified at 0°. It was dried on tile at 0°, recrystallized from aqueous methanol and again distilled (30%), m.p. 47°–49° C.

Anal. Calcd. for $C_{13}H_{21}O_2N$; C, 69.92; H, 9.48; N, 6.27. Found: C, 70.00; H, 9.42; N, 6.12.

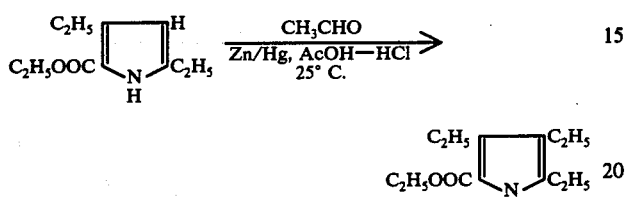

The previous Examples were effected on a preparative scale. The following Examples were effected on a micro scale (1 mg). In the following Examples the following procedure was adopted.

The ether used was reagent grade anhydrous ether washed twice with acidified aqueous ferrous sulfate, three times with water, then stirred 15 min with anhydrous $MgSO_4$; it was then diluted and the center 60% was stored < 10 days in the dark at 0°.

Diazomethane: distilled ethereal diazomethane, from N-nitroso-p-toluenesulfonylmethylamide using Carbitol, (trademark for diethylene glycol monoethyl ether) was stirred magnetically at 0° with ½ volume of concentrated aqueous ammonia for 20 min. The ether layer was stored at 0° in the dark over KOH (1 pellet/2 ml) for less than 1 week. Solutions < ca. 0.5 M gave lower yields of esters.

The paraformaldehyde gave no trouble but some lots of paraldehyde were rejected because they gave peaks in the blank; no specimens of propionaldehyde or para-propionaldehyde were consistently satisfactory in this respect.

Acetic acid (Anachemia reagent, 1.0 ml) then hydriodic acid ("AnalR" (Trademark) 66%, stored at 0° C. but not decolorized, 0.5 ml) were added to the carbethoxypyrrole (1 mg) in a 1.5 ml flask fitted with a stirring bar and a reflux condenser. The flask was then placed in a pre-heated oil-bath and stirred magnetically. Carbethoxy derivatives of the sensitive 2,5-dialkylpyrroles were heated at 45 min at 90° C; all others for 1.5 h at 105°–110° C.

Paraformaldehyde (3 mg) or 0.01 ml of paraldehyde (or other aldehyde) were added to the cooled mixture. The mixture was then heated again at 105°–110° C. for 30 min or, when β-free pyrroles present were difficult to alkylate, 1 h. However, if methylated pyrrole esters were to be chromatographed, the mixture was heated for 30 min at 50° C.; a higher temperature resulted in lower yields and sometimes in an extra peak (r.r.t. relative retention time 2.25) in the chromatograms.

The solution was decolorized with the minimum amount of phosphonium iodide (a few mg), starting the reaction by returning the flask to the oil-bath for a few seconds.

The flask was fitted with a reflux condenser modified to trap the distillate, cooled, and placed in a 20° C. oil-bath. The solvent was removed at 5–10 mm with magnetic stirring as the bath was raised to 65°–70° C over 30 min. Only a film or a very little oil should remain on the walls of the flask or the yield will be lowered. When the products had been propylated some extra peaks were minimized when the residue at this stage was kept 1 h at 65° C and 0.05 mm. The flask was cooled in ice, and NaOH (1 ml of 10%) was added.

If the products were purely alkyl pyrroles there were extracted with 3 × 1 ml of ether at pH < 10. The ether extracts were placed in a chilled tube and centrifuged (5 min), transferred to a 10 ml conical flask, and swirled at intervals over 15 min with anhydrous $MgSO_4$ (40 mg). The ether was transferred to a pear-shaped flask and removed at room temperature under a partial vacuum; unless care is taken, the more volatile pyrroles may be lost here. The residue was dissolved in ether (1.0 mm) and 2μl of the ether solution was applied to the column for g.l.p.c.

When the products were pyrrole-propionic acids, the flask containing the alkaline solution was placed in an ice-bath and stirred magnetically. Phosphoric acid (ca. 1 ml of 1 vol 85%: 4 vol of water) was added until the mixture just began to turn congo red to black, and the pyrrole acids were extracted with 3 × 1 ml ether at pH 4.0. The extract was clarified by centrifuging for 10 min and the ether was then evaporated. The residue was dried for 30 min (40° C., 2 mm) then dissolved in 5 ml of ether containing 5 drops of methanol. Etheral diazomethane (1 ml) was added, and the solution was kept in the dark for 45 min. The ether was then evaporated, the residue dissolved in 0.5 ml of ether, and 5μl of the solution were applied to the column for g.l.p.c.

In each of the following Examples the reactants are stated and the reaction sequence set forth as well as the product obtained.

EXAMPLE 82

2,4,5-Trimethyl-3-carbethoxy-pyrrole was reductively alkylated using paraformaldehyde to yield tetramethyl pyrrole.

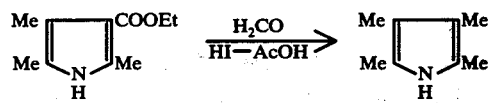

EXAMPLE 83

3-Carbethoxy-4,5-dimethyl-2-ethyl-pyrrole was reductively alkylated with paraformaldehyde to yield 2-ethyl-3,4,5-trimethyl pyrrole.

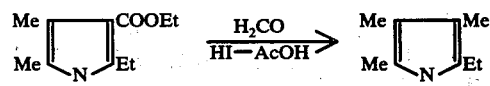

EXAMPLE 84

2-Carbethoxy-3,4-dimethyl-5-ethyl-pyrrole was reductively alkylated with paraldehyde to yield 2,5-diethyl-3,4 dimethyl-pyrrole.

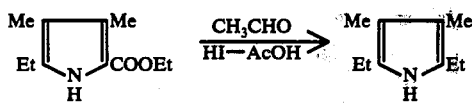

EXAMPLE 85

2,4-Dimethyl-3-ethyl-5-carbethoxy-pyrrole was reductively alkylated with paraformaldehyde to yield 3-ethyl-2,4,5-trimethyl-pyrrole.

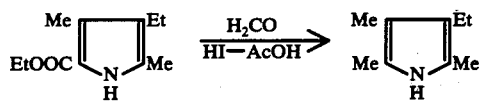

EXAMPLE 86

2-Carbethoxy-4,5-dimethyl-pyrrole was reductively alkylated with paraldehyde to yield 2,3-dimethyl-4,5-diethyl-pyrrole.

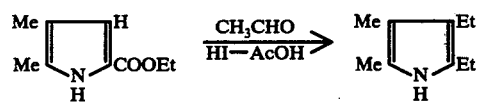

EXAMPLE 57

2-n-propyl-3-carbethoxy-4,5-dimethyl-pyrrole was reductively alkylated with paraldehyde to yield 2-n-propyl-3-ethyl-4,5-dimethyl-pyrrole.

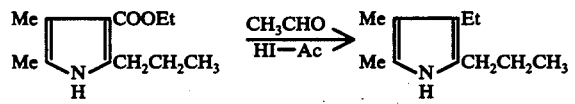

EXAMPLE 88

2,4-Dimethyl-3-ethyl-5-carbethoxy-pyrrole was reductively alkylatd with paraldehyde to yield 2,4-dimethyl-3,5-diethyl-pyrrole.

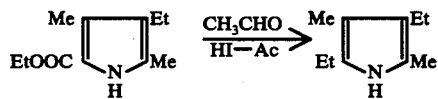

EXAMPLE 89

2,5-Diethyl-3-carbethoxy-4-methyl-pyrrole was reductively alkylated with paraldehyde to yield 2,3,5-diethyl-4-methyl-pyrrole.

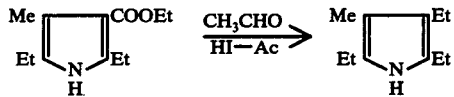

EXAMPLE 90

2-Carbethoxy-3,5-diethyl-4-methyl-pyrrole was reductively alkylated with propionaldehyde to yield 2-n-propyl-3,5-diethyl-4-methylpyrrole.

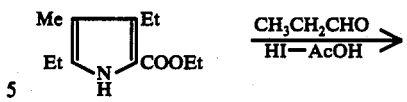

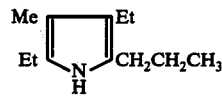

EXAMPLE 91

2,5-Dimethyl-3-carbethoxy pyrrole was reductively alkylated with paraldehyde to yield 2,5-dimethyl-3,4-diethyl-pyrrole.

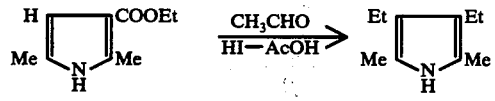

EXAMPLE 92

2,3-Diethyl-4-carbethoxy-5-methyl-pyrrole was reductively alkylated with paraldehyde to yield 2,3,4-triethyl-5-methyl-pyrrole.

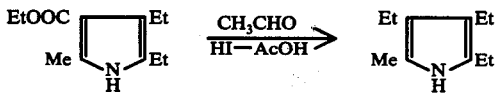

EXAMPLE 93

2,5-Diethyl-3-carbethoxy-pyrrole was reductively alkylated with paraldehyde to yield tetraethyl-pyrrole.

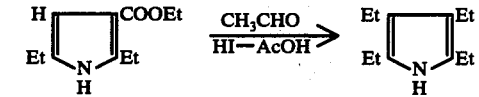

EXAMPLE 94

2-Carbethoxy-3-n-propyl-4,5-dimethyl-pyrrole was reductively alkylated with paraformaldehyde to yield 2,4,5-trimethyl-3-n-propyl-pyrrole.

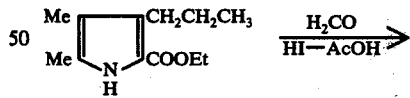

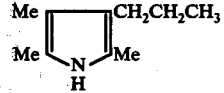

EXAMPLE 95

2-Ethyl-3-n-propyl-4-methyl-5-carbethoxy-pyrrole was reductively alkylated with paraformaldehyde to yield 2-ethyl-3-n-propyl-4,5-dimethylpyrrole.

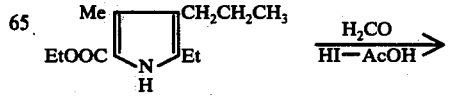

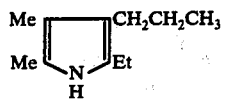

EXAMPLE 96

2,3-di-(n-propyl)-4-methyl-5-carbethoxy-pyrrole was reductively alkylated with paraformaldehyde to yield 2,3-di-(n-propyl)-4,5-dimethyl-pyrrole.

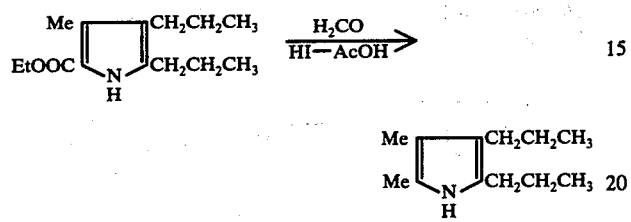

EXAMPLE 97

2,4-Dimethyl-3-isopropyl-5-carbethoxy-pyrrole was reductively alkylated with paraformaldehyde to yield 2,4,5-trimethyl-3-isopropyl-pyrrole.

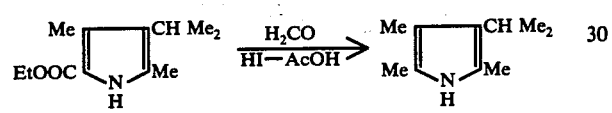

EXAMPLE 98

2,4-Dimethyl-3-isobutyl-5-carbethoxy-pyrrole was reductively alkylated with paraformaldehyde to yield 2,4,5-trimethyl-3-isobutyl-pyrrole.

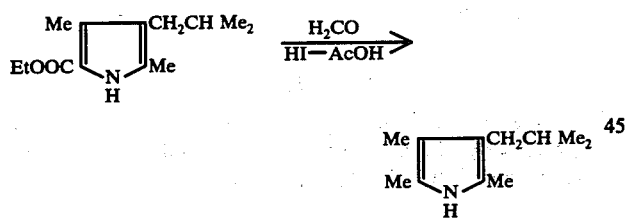

EXAMPLE 99

2,4-Dimethyl-3(α methyl n-propyl)-5-carbethoxy-pyrrole was reductively alkylated with paraformaldehyde to yield 2,4,5-trimethyl-3-(αmethyl n-propyl)pyrrole.

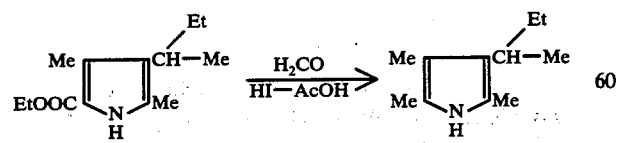

EXAMPLE 100

2-Carbethoxy-3-methyl-4,5-cyclopropyl-pyrrole was reductively alkylated with paraformaldehyde to yield 2,3-dimethyl-4,5-cyclopropylpyrrole.

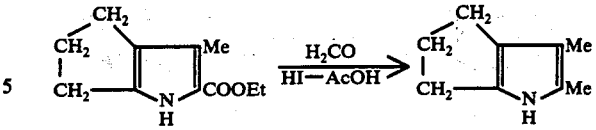

EXAMPLE 101

2-Carbethoxy-3-ethyl-4,5-cyclopropyl-pyrrole was reductively alkylated with paraformaldehyde to yield 2-methyl-3-ethyl-4,5-cyclopropylpyrrole.

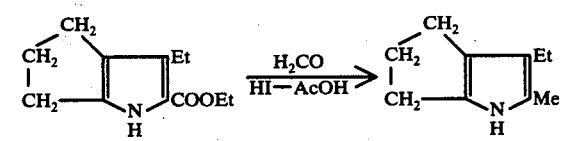

EXAMPLE 102

2,4-Dimethyl-3-ethyl-4-carbethoxy-pyrrole was reductively alkylated with propionaldehyde to yield 2,4-dimethyl-3-ethyl-5-n-propylpyrrole.

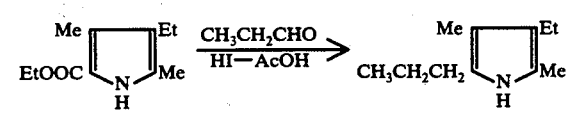

EXAMPLE 103

2-n-propyl-3-ethyl-4-methyl-5-carbethoxy-pyrrole was reductively alkylated with propionaldehyde to yield 2,5-di(n-propyl)-3-ethyl-4-methylpyrrole.

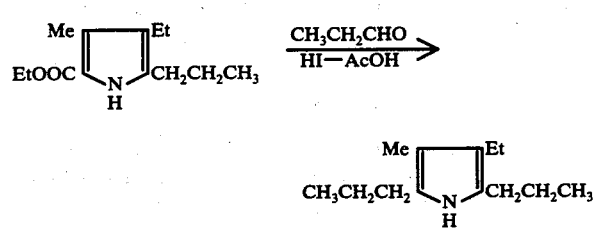

EXAMPLE 104

2-Carbethoxy-3,5-di(n-propyl)-4-methyl-pyrrole was reductively alkylated with paraformaldehyde to yield 2,4-dimethyl-3,5-di(n-propyl)-pyrrole.

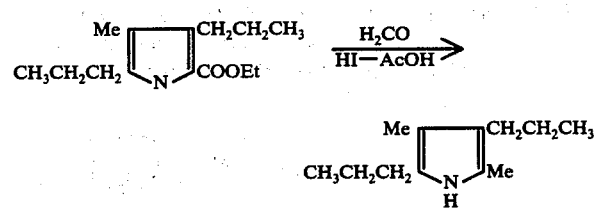

EXAMPLE 105

2-Carbethoxy-3,5-di(n-propyl)-4-methyl-pyrrole was reductively alkylated with paraldehyde to yield 2-ethyl-3,5-di(n-propyl)-4-methyl-pyrrole.

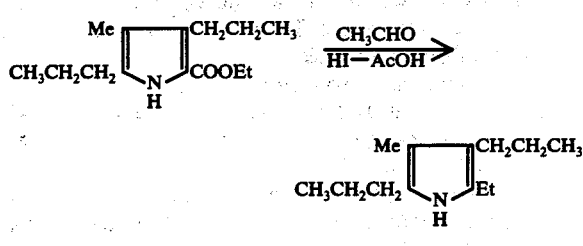

EXAMPLE 106

2,3-Di(n-propyl)-4-methyl-5-carbethoxy-pyrrole was reductively alkylated with propionaldehyde to yield 2,3,5-tri(n-propyl)-4-methyl-pyrrole.

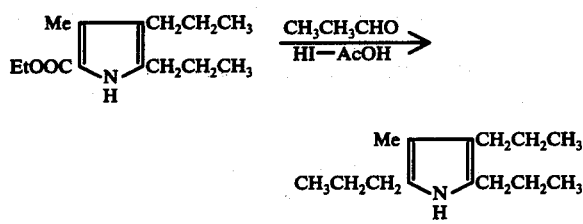

EXAMPLE 107

2-Carbethoxy-3-isobutyl-4,5-dimethyl-pyrrole was reductively alkylated with paraformaldehye to yield 2,4,5-trimethyl-3-isobutyl pyrrole.

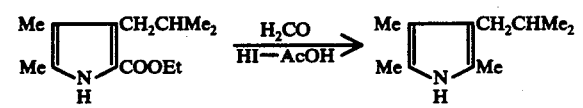

EXAMPLE 108

2-Ethyl-3-isobutyl-4-methyl-5-carbethoxy-pyrrole was reductively alkylated with paraformaldehye to yield 2-ethyl-3-isobutyl-4,5-dimethylpyrrole

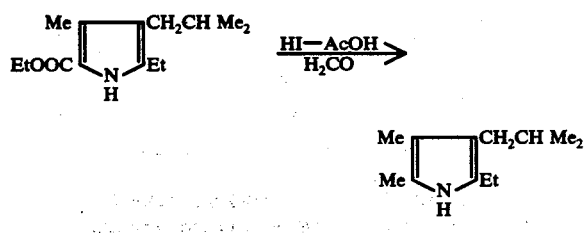

EXAMPLE 109

2-n-propyl-3-isobutyl-4-methyl-5-carbethoxy-pyrrole was reductively alkylated with paraformaldehyde to yield 2-n-propyl-3-isobutyl-4,5-di-methyl-pyrrole.

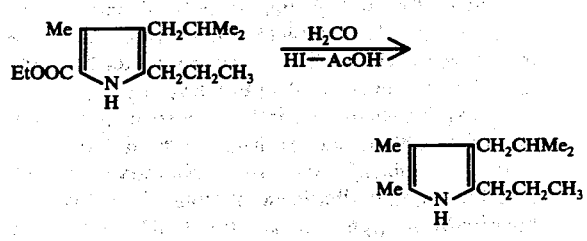

EXAMPLE 110

2,4-Dimethyl-3-carbethoxy ethyl-5-carbethoxy-pyrrole was reductively alkylated with paraformaldehyde to yield 2,4,5-trimethyl-3-carboxyethyl-pyrrole.

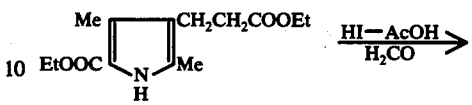

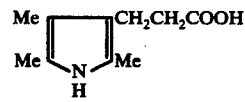

EXAMPLE 111

2-Ethyl-3-carbethoxy-ethyl-5-carbethoxy-pyrrols was reductively alkylated with paraformaldehyde to yield 2-ethyl-3-carboxyethyl-4,5-dimethyl-pyrrole.

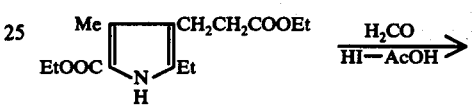

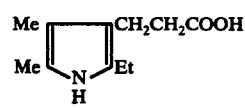

EXAMPLE 112

2-n-propyl-3-carbethoxyethyl-4-methyl-5-carbethoxy-pyrrole was reductively alkylated with paraformaldehyde to yield 2-n-propyl-3-carboxyethyl-4,5-dimethyl-pyrrole.

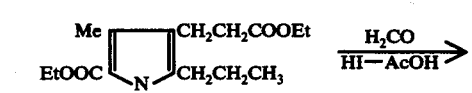

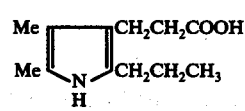

EXAMPLE 113

2-Carbethoxy-3-carbethoxyethyl-4-methyl-5-ethyl pyrrole was reductively alkylated with paraformaldehyde to yield 2,4-dimethyl-3-carboxyethyl-5-ethyl pyrrole.

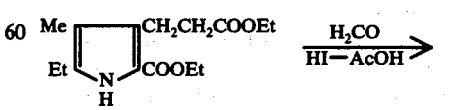

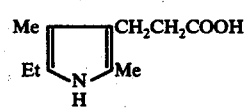

EXAMPLE 114

2-Carbethoxy-3-carbethoxyethyl-4-methyl-5-ethyl-pyrrole was reductively alkylated with paraldehyde to yield 2,5-diethyl-3-carboxyethyl-4-methyl-pyrrole.

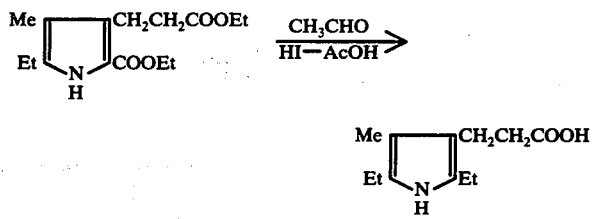

EXAMPLE 115

2-n-propyl-3-crbethoxyethyl-4-methyl-5-carbethoxy-pyrrole was reductively alkylated with paraldehyde to yield 2-n-propyl-3-carboxyethyl-4-methyl-5-ethyl-pyrrole.

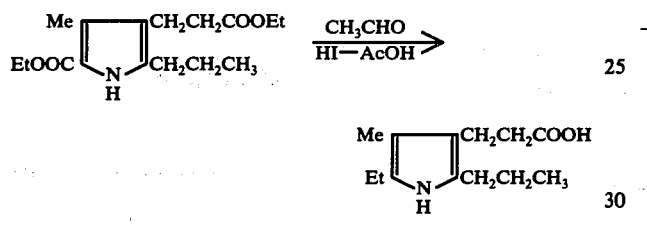

EXAMPLE 116

2-Carbethoxy-3-carbethoxyethyl-4-methyl-5-n-propyl-pyrrole was reductively alkylated with paraformaldehyde to yield 2,4-dimethyl-3-carboxyethyl-5-n-propyl-pyrrole.

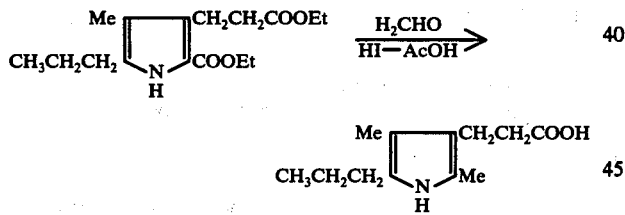

In Examples 111 through 116 the reaction in the presence of acetic acid and hydrogen iodide while splitting off the rug carbethoxy group merely hydrolyses the side chain carbethoxy group to yield a free carboxylic acid group. The free propionic acid obtained in these Examples in the reductive alkylation was esterified with diazomethane by the procedure set forth heretofore to enable improved identification by g.l.p.c.

In Examples 82 to 116 in which the preparations were on a microscale the products obtained were identified by g.l.p.c. (gas liquid phase chromatography) and by their relative retention times (rrt's) compared to standards. The procedure involved as is disclosed in an article entitled The Analytical Reduction of Pyrroles by R. A. Chapman et al Can. J. Chem. 49 pages 3544 to 3563 November 1971 incorporated herein by reference involves the use of a Pye Argon Chromatograph with glass columns packed with 0.5 × 117 cm of chromosorb G (acid washed and treated with D.M.C.S.) with 5% SE-30. In operation at the temperature specified the sample was quickly injected through the open top of the column and as close to the packing as possible when the gas flow was interrupted. The rrt's were measured from the start of the ether peak.

The column used was (A) operated at 75° C. at a pressure of about 12.1 psi using 2,4-dimethyl-3-ethyl-pyrrole as comparison standard or (B) operated at 100° C. with a flow rate of 158 ml/min at about 16 psi.

The column used was operated under one of the following conditions which is indicated by the letter in the following table.

A. 75° C. using 2,4-dimethyl-3-ethylpyrrole as comparison standard;

B. 100° C. using 2,4,5-trimethyl-3-ethylpyrrole as comparison standard;

C. 135° C. using 2,4,5-trimethyl-3-ethylpyrrole as comparison standard or

D. 135° C. using 2,4-dimethyl-3-carboxyethyl-pyrrole as standard.

The results obtained are shown in the following Table

| Example | Operating Conditions | RRT |
| --- | --- | --- |
| 82 | A | 1.18 |
| 83 | A | 1.86 |
| 84 | A | 2.76 |
| 85 | A | 1.85 |
| 86 | A | 2.95 |
| 87 | A | 5.04 |
| 88 | A | 2.84 |
| 89 | A | 4.27 |
| 90 | B | 3.15 |
| 91 | A | 2.92 |
| 92 | A | 4.60 |
| 93 | A | 6.94 |
| 94 | A | 3.41 |
| 95 | A | 5.24 |
| 96 | A | 8.77 |
| 97 | A | 2.99 |
| 98 | A | 4.86 |
| 99 | A | 4.68 |
| 100 | A | 3.74 |
| 101 | A | 6.27 |
| 102 | B | 2.26 |
| 103 | B | 4.49 |
| 104 | B | 3.80 |
| 105 | B | 5.10 |
| 106 | B | 8.00 |
| 107 | A | 4.86 |
| 108 | C | 2.71 |
| 109 | C | 3.79 |
| 110 | D | 1.52 |
| 111 | D | 2.02 |
| 112 | D | 2.83 |
| 113 | D | 2.00 |
| 114 | D | 2.59 |
| 115 | D | 3.56 |
| 116 | D | 2.73 |

The embodiments of the invention in which an exclusive property or privilege is claimed are defined as follows:

1. A single step method of ring alkylating a substituted pyrrole compound which comprises the steps of reacting in a liquid system (1) a substituted pyrrole compound selected from the group consisting of 2,4-dimethyl-5-carbethoxy pyrrole, 2,4-dimethyl-3,5-dicarbethoxy pyrrole, 2-methyl-3-carbethoxy pyrrole, 2,4-dimethyl-3-acetyl pyrrole, 2-carbethoxy-3-methyl-pyrrole, 2-methyl-5-carbethoxy pyrrole, 2,3-dimethyl-5-carbethoxy pyrrole, 2,4-dimethyl-3-bromo-5-carbethoxy pyrrole, 3-ethyl-4-methyl-5-carbethoxy pyrrole, 3-methyl-4-carbethoxy pyrrole, 2,5-dimethyl-3-carbethoxy pyrrole, 2-methyl-3,5-dicarbethoxy pyrrole, 3-methyl-2,5-dicarbethoxy pyrrole, 2,3-dimethyl-5-carbethoxy pyrrole, 2,3-dimethyl pyrrole, 2,5-dimethyl pyrrole, 2-methyl-5-carboxy pyrrole-4-propionic acid diethyl ester and 2,4-dimethyl pyrrole; with (2) a carbonyl compound selected from the group consisting of formaldehyde, acetaldehyde, propionaldehyde, n-butyraldehyde, isobutyraldehyde, paraldehyde, heptaldehyde, laurylaldehyde, stearaldehyde, amino-acetaldehyde, acetone, diethyl-ketone, isobutyl-methyl ketone, 3-pentanone, cyclopentanone, cyclohexanone, pyruvic acid, levulinic acid, glyoxylic acid, benzaldehyde acetophenone, chloroacetone, 2,5-hexane dione and 2-formyl-3-acetyl-4-methyl-5-carbethoxy-pyrrole in the presence of both (a) an acid condensing agent selected from the group consisting of hydriodic acid, aqueous HI, HI in acetic acid, HI in heptane, HBr in acetic acid HCl in acetic acid, $H_2SO_4$ in acetic acid, hydrobromic acid, sulfuric acid, and hydrochloric acid; and (b) a reducing agent selected from the group consisting of hydrogen iodide, zinc, zinc in acid, zinc amalgam, stannous bromide, and stannous chloride and when said reducing agent is hydrogen iodide, there may be included also an auxiliary substance selected from the group consisting of red phosphorus, phosphonium iodide, and hypo-phosphorous acid at a temperature sufficient to effect reaction between the substituted pyrrole compound (1) and said carbonyl compound (2)

whereby to form from the reactants a derivative of said pyrrole compound in which the carbon of said carbonyl group is attached to the pyrrole ring.

2. A single step method of ring alkylating a substituted pyrrole compound which comprises the steps of reacting in a liquid system (1) a substituted pyrrole compound selected from the group consisting of 2,4-dimethyl-5-carbethoxy pyrrole, 2,4-dimethyl-3,5-dicarbethoxy pyrrole, 2-methyl-3 carbethoxy pyrrole, 2,4-dimethyl-3-acetyl pyrrole, 2-carbethoxy-3-methyl-pyrrole, 2-methyl-5-carbethoxy pyrrole, 2, 3-dimethyl-5-carbethoxy pyrrole, 2,4-dimethyl-3-bromo-5-carbethoxy pyrrole, 3-ethyl-4-methyl-5-carbethoxy pyrrole, 3-methyl-4-carbethoxy pyrrole, 2,5-dimethyl-3-carbethoxy pyrrole, 2-methyl-3,5-dicarbethoxy pyrrole, 3-methyl-2,5-dicarbethoxy pyrrole, 2,3-dimethyl-5-carbethoxy pyrrole, 2,3-dimethyl pyrrole, 2,5-dimethyl pyrrole, 2-methyl-5-carboxy pyrrole-4-propionic acid diethyl ester and 2,4-dimethyl pyrrole with (2) a carbonyl compound generated in situ from paraformaldehyde or paraldehyde in the presence of both (a) an acid condensing agent selected from the group consisting of hydriodic acid, aqueous HI, HI in acetic acid, HI in heptane, HBr in acetic acid HCl in acetic acid, $H_2SO_4$ in acetic acid, hydrobromic acid, sulfuric acid, and hydrochloric acid; and (b) a reducing agent selected from the group consisting of hydrogen iodide, zinc, zinc in acid, zinc amalgam, stannous bromide, and stannous chloride and when said reducing agent is hydrogen iodide, there may be included also an auxiliary substance selected from the group consisting of red phosphorus, phosphonium iodide, and hypo-phosphorous acid at a temperature sufficient to effect reaction between the substituted pyrrole compound (1) and said carbonyl compound (2)

whereby to form from the reactants a derivative of said pyrrole compound in which the carbon of said carbonyl group is attached to the pyrrole ring.

3. A method as claimed in claim 1 in which the pyrrole compound is a pyrrole substituted by at least one methyl group.

4. A method as claimed in claim 1 in which the pyrrole compound is a pyrrole substituted by two methyl groups.

5. A method as claimed in claim 1 in which the condensing agent is selected from aqueous HI, HI in acetic acid, HI in heptane, HBr in acetic acid, HCl in acetic acid or $H_2SO_4$ in acetic acid.

6. A method as claimed in claim 1 in which the reducing agent is hydriodic acid, a mixture of hydriodic acid and phosphonium iodide, hydriodic acid and red phosphorous, a mixture of HI and hypophosphorous acid, zinc in acid, stannous bromide or stannous chloride.

7. A method as claimed in claim 1 in which the condensing agent and reducing agent is hydriodic acid.

* * * * *